(12) United States Patent
Crawford et al.

(10) Patent No.: US 10,172,993 B2
(45) Date of Patent: Jan. 8, 2019

(54) WAVE-BASED PATIENT LINE BLOCKAGE DETECTION

(71) Applicant: Fresenius Medical Care Holdings, Inc., Waltham, MA (US)

(72) Inventors: William Scott Crawford, Palo Alto, CA (US); Robert Matthew Ohline, Redwood City, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 212 days.

(21) Appl. No.: 15/098,632

(22) Filed: Apr. 14, 2016

(65) Prior Publication Data
US 2017/0296731 A1    Oct. 19, 2017

(51) Int. Cl.
| | | |
|---|---|---|
| *G01M 3/02* | (2006.01) | |
| *A61M 1/28* | (2006.01) | |
| *G01N 29/024* | (2006.01) | |
| *G01N 29/30* | (2006.01) | |
| *A61M 5/168* | (2006.01) | |

(52) U.S. Cl.
CPC .............. *A61M 1/285* (2013.01); *A61M 1/28* (2013.01); *G01N 29/024* (2013.01); *G01N 29/30* (2013.01); *A61M 2005/16863* (2013.01); *A61M 2205/121* (2013.01); *A61M 2205/3331* (2013.01); *A61M 2205/70* (2013.01); *A61M 2209/02* (2013.01); *G01N 2291/011* (2013.01); *G01N 2291/042* (2013.01)

(58) Field of Classification Search
CPC ................. G01N 29/30; G01N 29/024; G01N 2291/011; G01N 2291/042; A61M 1/28; A61M 1/281; A61M 1/282; A61M 1/284; A61M 1/285; A61M 1/287; A61M 1/288; G01M 3/02

USPC ..... 73/1.83, 1.01, 1.57, 1.79, 1.81, 37, 37.5, 73/570, 584, 865.8, 432.1; 604/27–45, 604/4.01–6.14
See application file for complete search history.

(56) References Cited

U.S. PATENT DOCUMENTS

| | | |
|---|---|---|
| 5,438,510 A | 8/1995 | Bryant et al. |
| 5,906,589 A | 5/1999 | Gordon et al. |
| 6,485,263 B1 | 11/2002 | Bryant et al. |
| 8,167,832 B2 | 5/2012 | Bowman et al. |
| 8,486,005 B2 | 7/2013 | Yodfat et al. |

(Continued)

FOREIGN PATENT DOCUMENTS

WO    2015029039    3/2015

OTHER PUBLICATIONS

International Search Report and Written Opinion in International Application No. PCT/US2017/024673, dated Jun. 21, 2017, 20 pages (with English translation).

*Primary Examiner* — Robert R Raevis
(74) *Attorney, Agent, or Firm* — Fish & Richardson PC

(57) ABSTRACT

A dialysis machine (e.g., a peritoneal dialysis (PD) machine) can include a pressure sensor mounted at a proximal end of a patient line that provides PD solution to a patient through a catheter. During treatment, an occlusion can occur at different locations in the patient line and/or the catheter. Elastic waves may be generated at a pump that introduces (e.g., for fill cycles) or withdraws (e.g., for drain cycles) the solution into/out of the patient line. For example, when the solution is introduced or withdrawn suddenly, elastic waves travel distally down the patient line until they encounter the occlusion, and are then reflected back (e.g., toward the pressure sensor).

36 Claims, 34 Drawing Sheets

(56) References Cited

U.S. PATENT DOCUMENTS

2007/0270782 A1 11/2007 Miesel et al.
2008/0139996 A1 6/2008 Bowman et al.
2011/0106466 A1 5/2011 Furmanski et al.
2013/0046226 A1 2/2013 Suffritti et al.

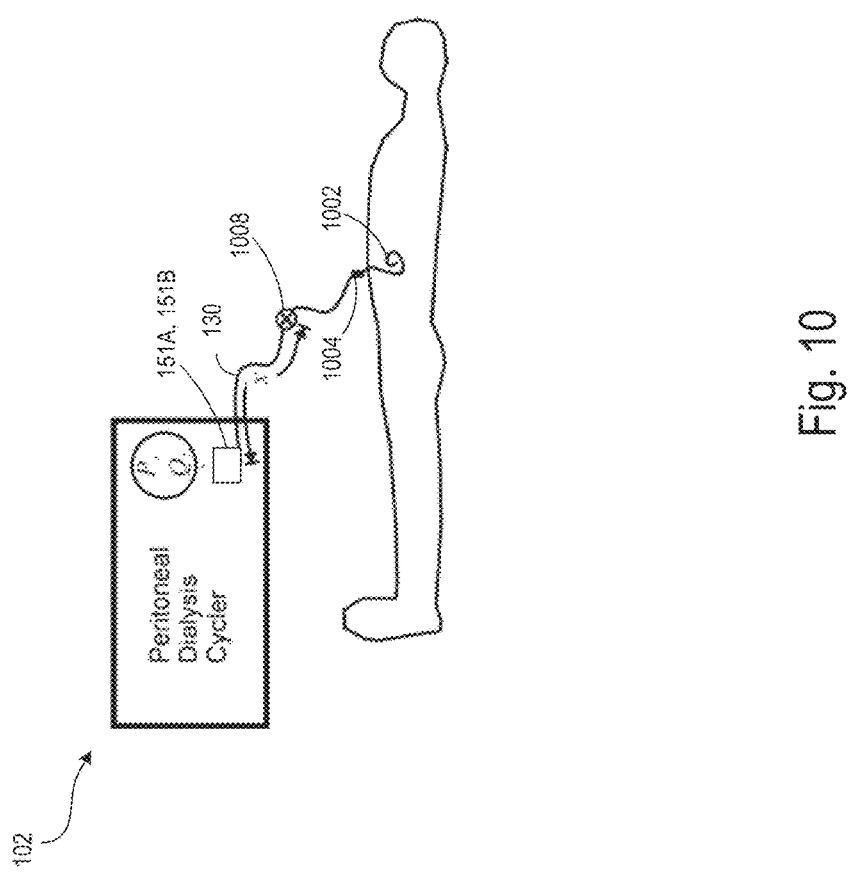

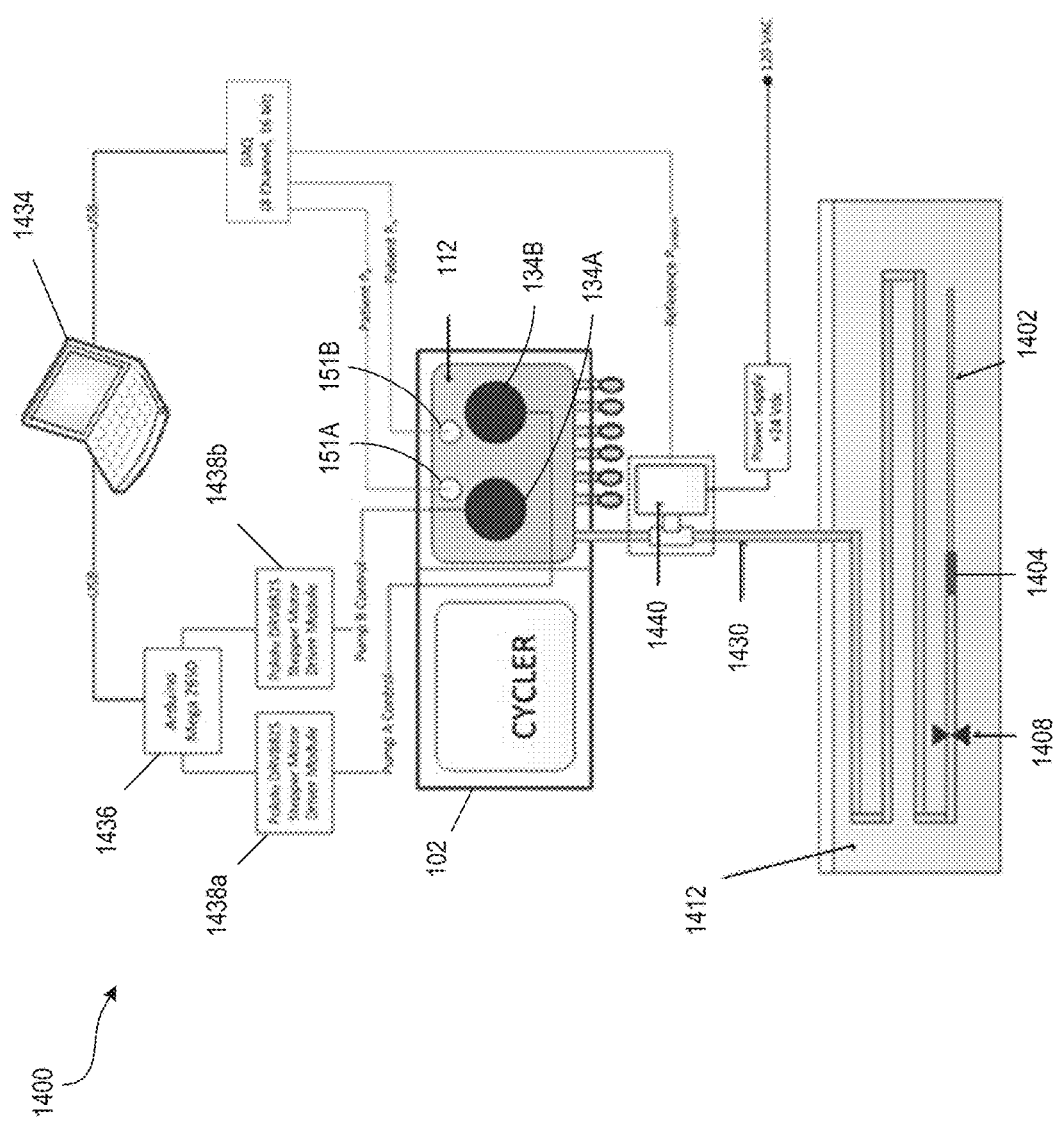

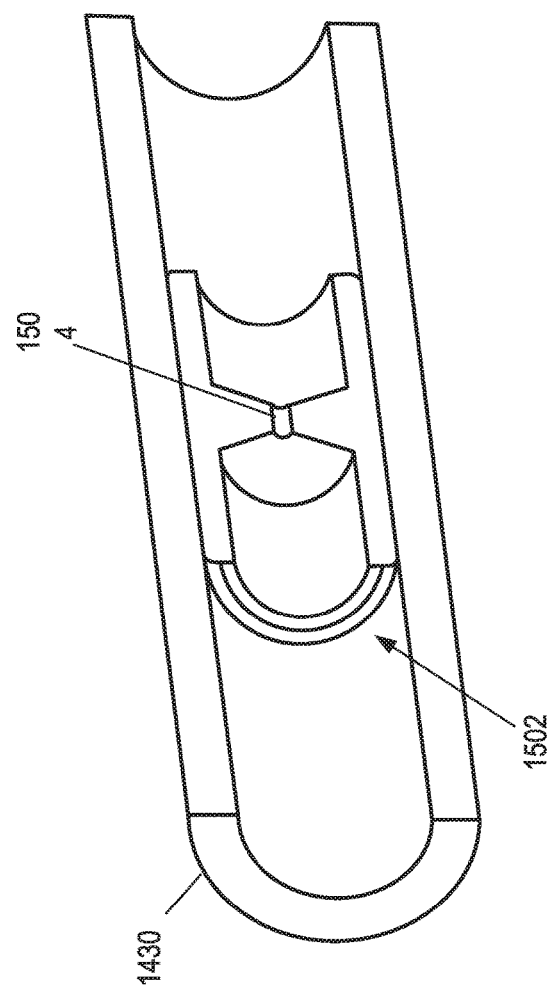

WAVE-BASED PATIENT LINE BLOCKAGE DETECTION

TECHNICAL FIELD

This disclosure relates to detecting a blockage in a patient line.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method includes measuring a first pressure at a proximal end of a medical tube connected to a medical device. The method also includes measuring a second pressure at the proximal end of the medical tube. The method also includes determining an elapsed time between the first pressure measurement and the second pressure measurement. The method also includes determining a location of an occlusion in the medical tube based on the elapsed time.

Implementations can include one or more of the following features.

In some implementations, the medical device includes a dialysis machine.

In some implementations, the dialysis machine includes a peritoneal dialysis (PD) machine.

In some implementations, at least one of the first pressure and the second pressure includes a local extremum of pressure measurements at the proximal end of the medical tube.

In some implementations, the local extremum includes at least one of a local maximum and a local minimum.

In some implementations, the first pressure and the second pressure are measured by a pressure sensor mounted at the proximal end of the medical tube.

In some implementations, the elapsed time represents a period of oscillations of an elastic wave.

In some implementations, the elastic wave originates from the proximal end of the medical tube.

In some implementations, the elastic wave is generated in response to at least one of an increase and a decrease in pressure in the medical tube.

In some implementations, a fluid flowing through the medical tube is at least partially blocked by the occlusion.

In some implementations, the fluid being at least partially blocked by the occlusion causes an increase or a decrease in pressure in the medical tube.

In some implementations, the at least one of an increase and a decrease in pressure is in response to a motion of a pump of the medical device.

In some implementations, the oscillations of the elastic wave are caused at least in part by the elastic wave being reflected back from the location of the occlusion.

In some implementations, the medical tube includes a catheter at a distal end of the medical tube.

In some implementations, the method also includes inferring a type of the occlusion based at least in part on the determined location of the occlusion.

In some implementations, the type of the occlusion includes one or more of a pinch of the medical tube, a kink in the medical tube, a deposit in the medical tube, and a deposit blocking a hole of a catheter at a distal end of the medical tube.

In some implementations, the deposit includes omental fat.

In some implementations, the method also includes determining the location of the occlusion in the medical tube based on the elapsed time and a wave speed of the elastic wave.

In some implementations, the wave speed of the elastic wave is based on one or more of dimensions of the medical tube, a material composition of the medical tube, and a density of a fluid flowing through the medical tube.

In some implementations, the wave speed of the elastic wave is empirically determined.

In some implementations, the method also includes performing a calibration prior to determining the location of the occlusion. The calibration is for determining a wave speed of an elastic wave propagating through the medical tube.

In some implementations, the calibration is for determining the wave speed of the elastic wave propagating through the medical tube for a particular medical tube and cassette configuration used in the medical device.

In another aspect, a method includes measuring a plurality of pressures at a proximal end of a medical tube connected to a medical device. The method also includes determining one or more elapsed times between local extrema of the measured pressures. The method also includes determining a location of an occlusion in the medical tube based on the one or more elapsed times.

Implementations can include one or more of the following features.

In some implementations, the local extrema include at least one of a local maximum and a local minimum.

In some implementations, the method also includes removing noise components from the measured pressures before determining the local extrema of the measured pressures.

In some implementations, the magnitudes of the pressure measurements decay over time when the occlusion is a partial occlusion.

In some implementations, the method also includes subtracting, from the measured pressures, values that approximate the decay of the pressure measurements as a result of the occlusion being a partial occlusion before determining the local extrema.

In some implementations, at least one of the local extrema of the measured pressures corresponds to an end of a pump motion that causes fluid to flow through the medical tube.

In some implementations, the method also includes determining an elapsed time between i) the end of the pump motion, and ii) an occurrence of a local extrema that occurs after the end of the pump motion. The method also includes determining the location of the occlusion based on the elapsed time.

In some implementations, the elapsed time represents a first half-wave period of oscillations of an elastic wave generated in response to at least one of an increase and a decrease in pressure in the medical tube.

In some implementations, the method also includes performing one or more signal processing techniques on the measured pressures.

In another aspect, a method includes measuring a first pressure at a proximal end of a medical tube connected to a medical device. The medical tube includes a plurality of zones. The method also includes measuring a second pressure at the proximal end of the medical tube. The method also includes determining an elapsed time between the first pressure measurement and the second pressure measurement. The method also includes determining in which of the plurality of zones an occlusion is located based on the elapsed time.

Implementations can include one or more of the following features.

In some implementations, the medical tube includes five zones.

In some implementations, the medical tube includes a catheter at a distal end of the medical tube. At least one of the zones includes the catheter.

In some implementations, the medical tube includes a port connecting the catheter to the medical tube. At least one of the zones includes the port.

In another aspect, a medical device includes a medical tube having a proximal end connected to an outlet of the medical device. The medical device also includes a pressure sensor mounted at the proximal end of the medical tube. The pressure sensor is configured for measuring a first and second pressure at the proximal end of the medical tube. The medical device also includes a processor configured for determining an elapsed time between the first pressure measurement and the second pressure measurement. The processor is also configured for determining a location of an occlusion in the medical tube based on the elapsed time.

Implementations can include one or more of the following features.

In some implementations, the medical device includes a dialysis machine.

In some implementations, the medical device includes a peritoneal dialysis machine.

Implementations can include one or more of the following advantages.

In some implementations, the systems and techniques described herein can be used to determine a location of an occlusion in the medical tube (e.g., in a patient line or in the catheter). In some examples, the type of occlusion can be inferred based on the determined location. The dialysis machine can determine an appropriate response for addressing the particular type of occlusion, including emitting an alert indicating the presence of the occlusion and/or adjusting one or more operating parameters of the dialysis machine in an attempt to clear the occlusion and/or to modulate the flow in the medical tube to avoid an overpressure condition.

In some implementations, the use of elastic waves for determining the location of the occlusion allows the methods described herein to be insensitive to hydrostatic effects (e.g., which would have a greater effect on methods that are based on pressure-flow relationships in the fluid).

In some implementations, the dialysis machine is configured to determine the location of the occlusion using the pressure sensor built into the dialysis machine without requiring a separate pressure sensor.

Other aspects, features, and advantages of the invention will be apparent from the description and drawings, and from the claims.

DESCRIPTION OF DRAWINGS

FIG. 10 shows a schematic diagram of the PD cycler of FIG. 1 connected to a patient.

FIG. 14 shows a schematic of a dialysis system that includes a PD machine.

FIG. 15 shows a cross-sectional view of an example partial internal occlusion.

Like reference symbols in the various drawings indicate like elements.

DETAILED DESCRIPTION

A dialysis machine (e.g., a peritoneal dialysis (PD) machine) can include a pressure sensor mounted at a proximal end of a patient line that provides PD solution to a patient through a catheter. During treatment, an occlusion (e.g., a partial occlusion or a complete occlusion) can occur at different locations in the patient line and/or the catheter. Elastic waves may be generated at a pump that introduces (e.g., for fill cycles) or withdraws (e.g., for drain cycles) the solution into/out of the patient line. For example, when the solution is introduced or withdrawn suddenly, elastic waves travel distally down the patient line until they encounter the occlusion, and are then reflected back (e.g., toward the pressure sensor). Utilizing principles of elastic wave theory, the location of the occlusion relative to the pressure sensor can be determined. For example, if the speed and the transit time of the wave are known, the distance that the wave traveled can be determined.

For a patient line of uniform properties, outgoing and reflected waves will travel at a common speed. This speed can be analytically predicted if the elastic properties and cross-sectional dimensions of the tubing are known, as well as determined based on empirical data. The transit time of the wave can be determined based on elapsed times between local extrema (e.g., local maxima or minima) of pressure measurements made by the pressure sensor. For example, oscillations in the measured pressure values as a result of the waves being reflected can be determined, and a period of such oscillations can be measured. The period (e.g., the transit time of the wave) can be multiplied by the speed of the wave to determine the distance traveled (e.g., from the pressure sensor, to the occlusion, and back to the pressure sensor), and the distance can be divided by two to determine the location of the occlusion relative to the location of the pressure sensor. Because some types of occlusions typically occur in certain parts of the patient line, the occlusion type can often be inferred based on the determined location.

The use of elastic waves for determining the location of the occlusion allows the methods described herein to be insensitive to hydrostatic effects, which would have a greater effect on methods that are based on pressure-flow relationships in the fluid. Further, the methods described herein operate in the frequency domain. Thus, provided that waves have sufficient amplitude for accurate detection, the results are relatively insensitive to amplitude-attenuating effects that may vary from case to case.

Figure 1:
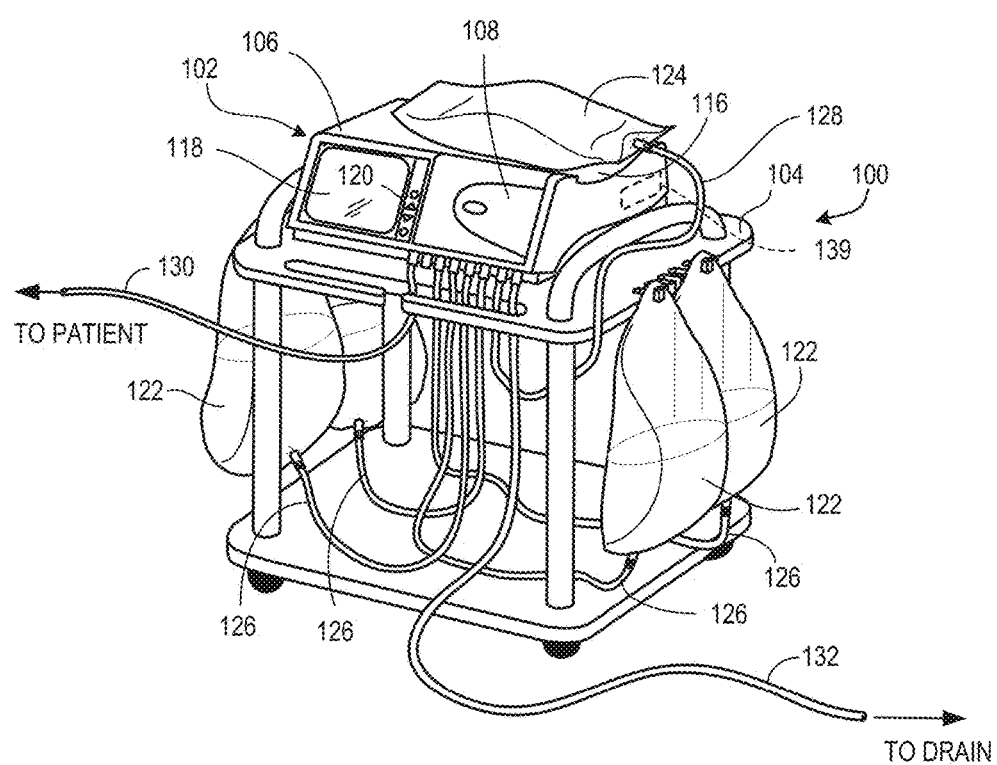
FIG. 1 shows an example of a peritoneal dialysis (PD) system.
Figure 2:
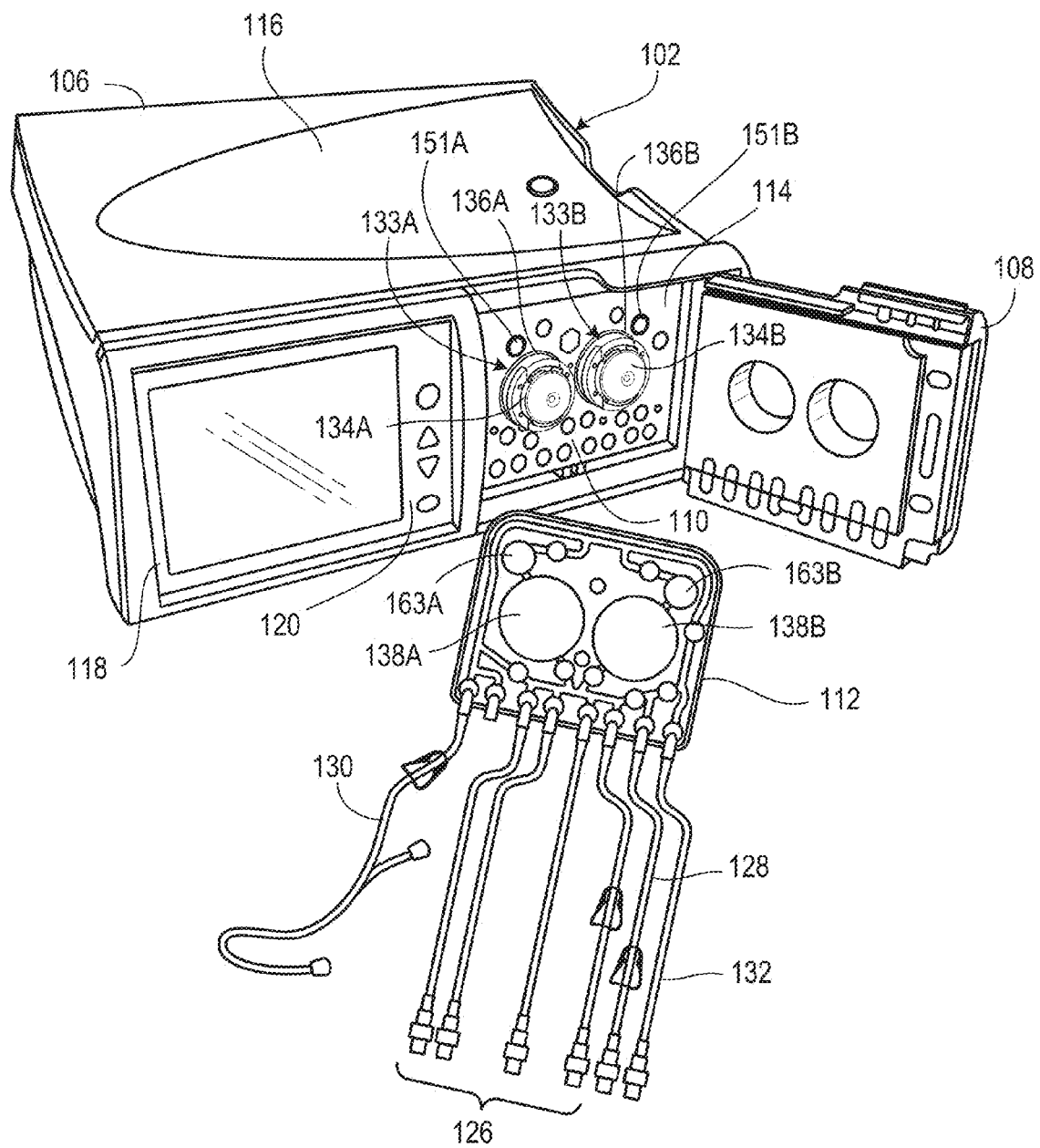
FIG. 2 is a perspective view of a PD cycler and a PD cassette of the PD system of FIG. 1, with a door of the PD cycler in the open position to show the inner surfaces of the PD cycler that interface with the PD cassette during use.

FIG. 1 shows a PD system 100 that includes a PD machine (also generally referred to as a PD cycler) 102 seated on a cart 104. Referring also to FIG. 2, the PD machine 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter (e.g., the catheter 1002 of FIG. 10) and can be used to pass dialysate back and forth between the cassette 112 and the patient's peritoneal cavity during use. The catheter 1002 may be connected to the patient line 130 via a port (1004 of FIG. 10) such as a fitting. The drain line 132 can be connected to a drain or drain receptacle and can be used to pass dialysate from the cassette 112 to the drain or drain receptacle during use.

The PD machine 102 also includes a control unit 139 (e.g., a processor). The control unit 139 can receive signals from and transmit signals to the touch screen display 118, the control panel 120, and the various other components of the PD system 100. The control unit 139 can control the operating parameters of the PD machine 102. In some implementations, the control unit 139 is an MPC823 PowerPC device manufactured by Motorola, Inc.

Figure 3:
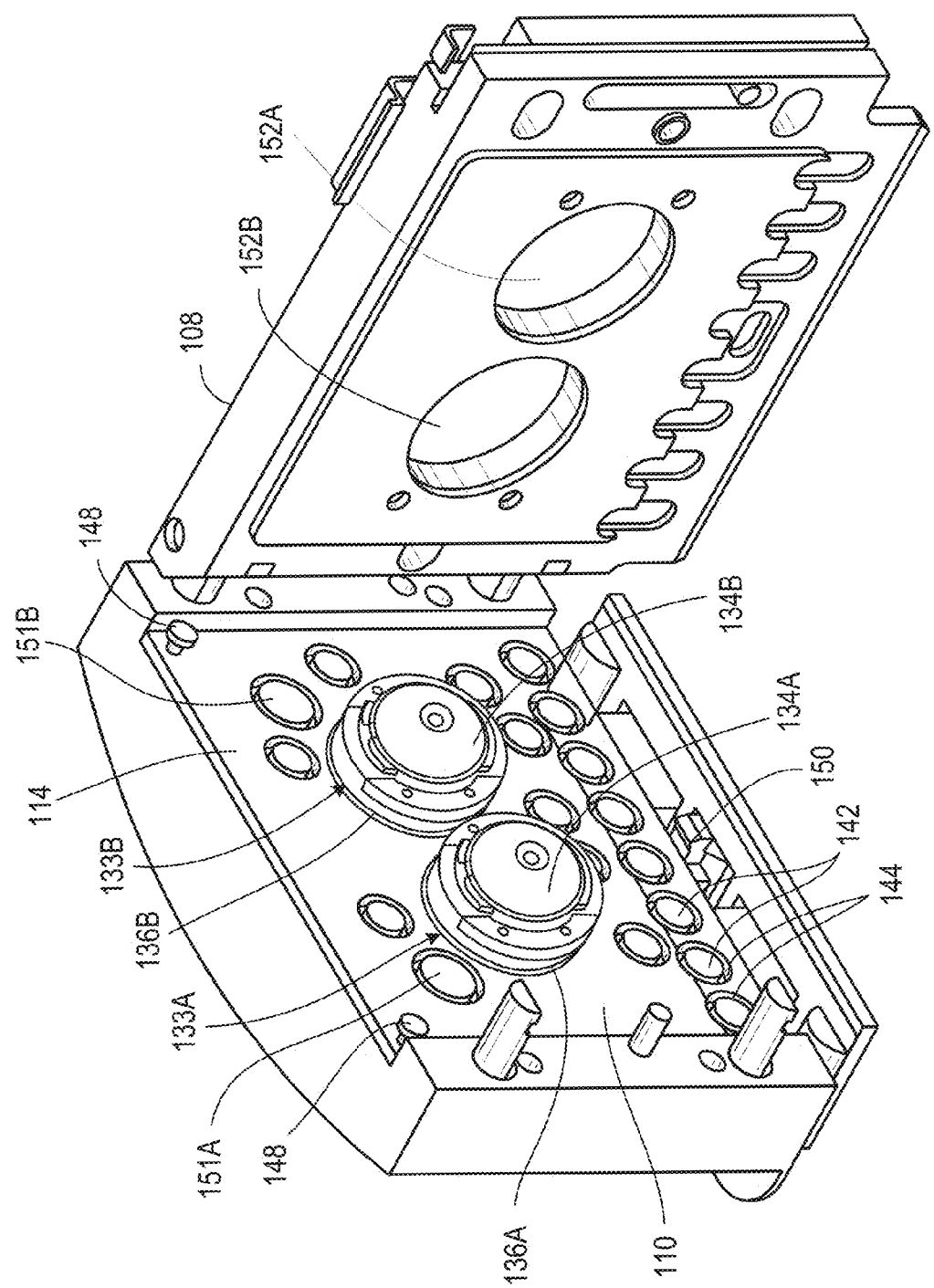
FIG. 3 is a perspective view of an open cassette compartment of the PD cycler of FIG. 1.

FIG. 3 shows a more detailed view of the cassette interface 110 and the door 108 of the PD machine 102. As shown, the PD machine 102 includes pistons 133A, 133B with piston heads 134A, 134B attached to piston shafts 135A, 135B (piston shaft 135A shown in FIGS. 9A-G) that can be axially moved within piston access ports 136A, 136B formed in the cassette interface 110. The pistons 133A, 133B, piston heads 134A, 134B, and piston shafts 135A, 135B are sometimes referred to herein as pumps. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The stepper motors may be controlled by driver modules (e.g., the driver modules 1438a, 1438b of FIG. 14). The nuts, in turn, are connected to the pistons 133A, 133B and thus cause the pistons 133A, 133B to move inward and outward as the stepper motors rotate the lead screws. Stepper motor controllers (e.g., in communication with the microcontroller 1436 of FIG. 14) provide the necessary current to be driven through the windings of the stepper motors to move the pistons 133A, 133B. The polarity and sequencing of the current determines whether the pistons 133A, 133B are advanced or retracted. In some implementations, the stepper motors require 200 steps to make a full rotation, and this corresponds to 0.048 inch of linear travel (e.g., for a leadscrew with a given thread pitch).

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to accurately position the piston heads 134A, 134B of the pistons 133A, 133B.

As discussed below, when the cassette 112 (shown in FIGS. 2 and 4-7) is positioned within the cassette compartment 114 of the PD machine 102 with the door 108 closed, the piston heads 134A, 134B of the PD machine 102 align with pump chambers 138A, 138B of the cassette 112 such that the piston heads 134A, 134B can be mechanically connected to dome-shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIGS. 2, 4, 6, and 7) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B.

The pressure sensors 151A, 151B can be any sensors that are capable of measuring the fluid pressure in the sensing chambers 163A, 163B. In some implementations, the pressure sensors are solid state silicon diaphragm infusion pump force/pressure transducers. One example of such a sensor is the Model 1865 force/pressure transducer manufactured by Sensym Foxboro ICT. In some implementations, the force/pressure transducer is modified to provide increased voltage output. The force/pressure transducer can, for example, be modified to produce an output signal of 0 to 5 volts.

Still referring to FIG. 3, the PD machine 102 also includes multiple inflatable members 142 positioned within inflatable member ports 144 in the cassette interface 110. The inflatable members 142 align with depressible dome regions 146 of the cassette 112 (shown in FIGS. 4-6) when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions 146 of the cassette 112. The inflatable members 142 act as valves to direct dialysate through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102, as shown in FIG. 3, defines cylindrical recesses 152A, 152B that substantially align with the pistons 133A, 133B when the door 108 is in the closed position. When the cassette 112 (shown in FIGS. 4-7) is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

The control unit (139 of FIG. 1) is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. The control unit 139 monitors the components to which it is connected to determine whether any complications exist within the PD system 100, such as the presence of an occlusion.

Figure 4:
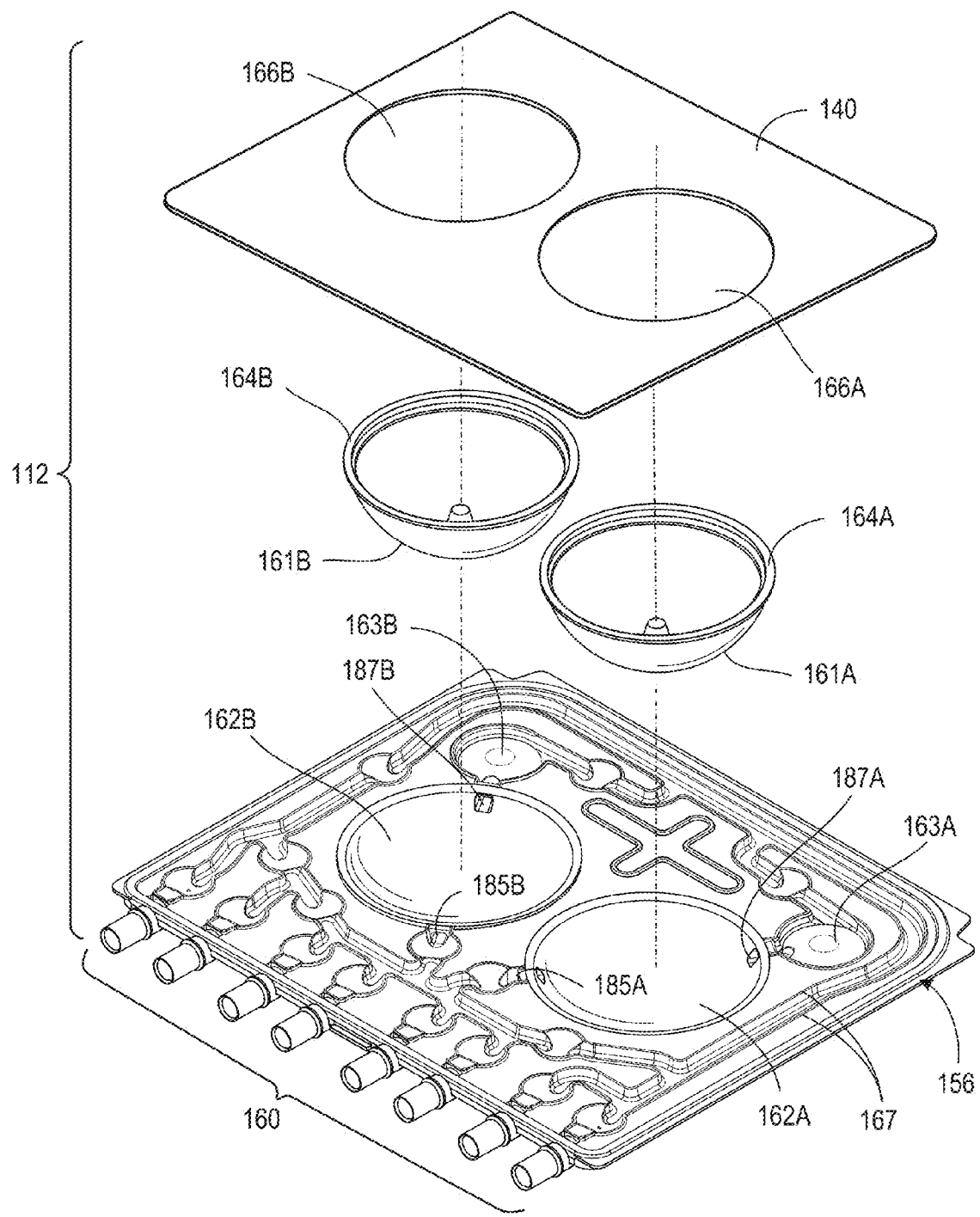
FIG. 4 is an exploded, perspective view of the PD cassette of FIG. 2, which includes dome-shaped fastening members that can be mechanically connected to piston heads of the PD cycler of FIG. 1.
Figure 5:
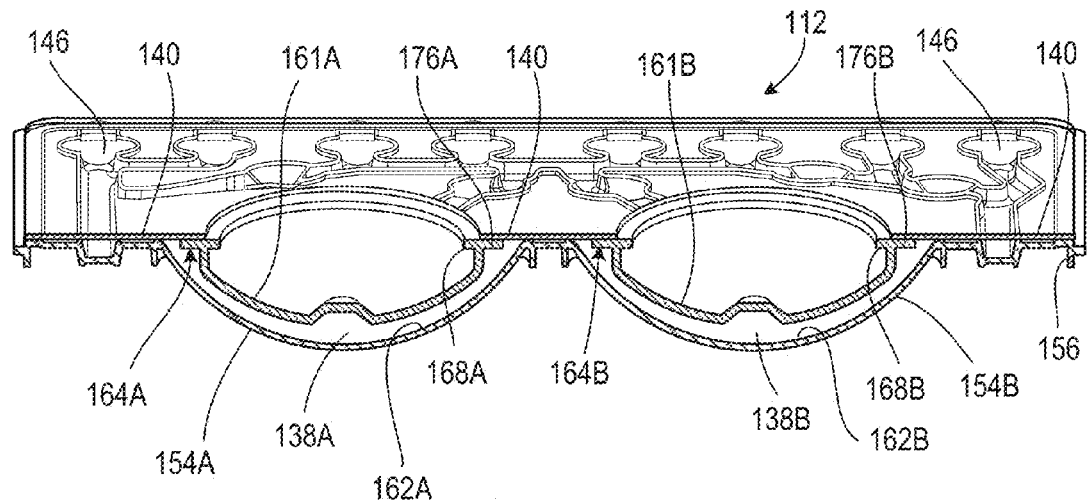
FIG. 5 is a perspective, cross-sectional view of the fully assembled PD cassette of FIG. 4.
Figure 6:
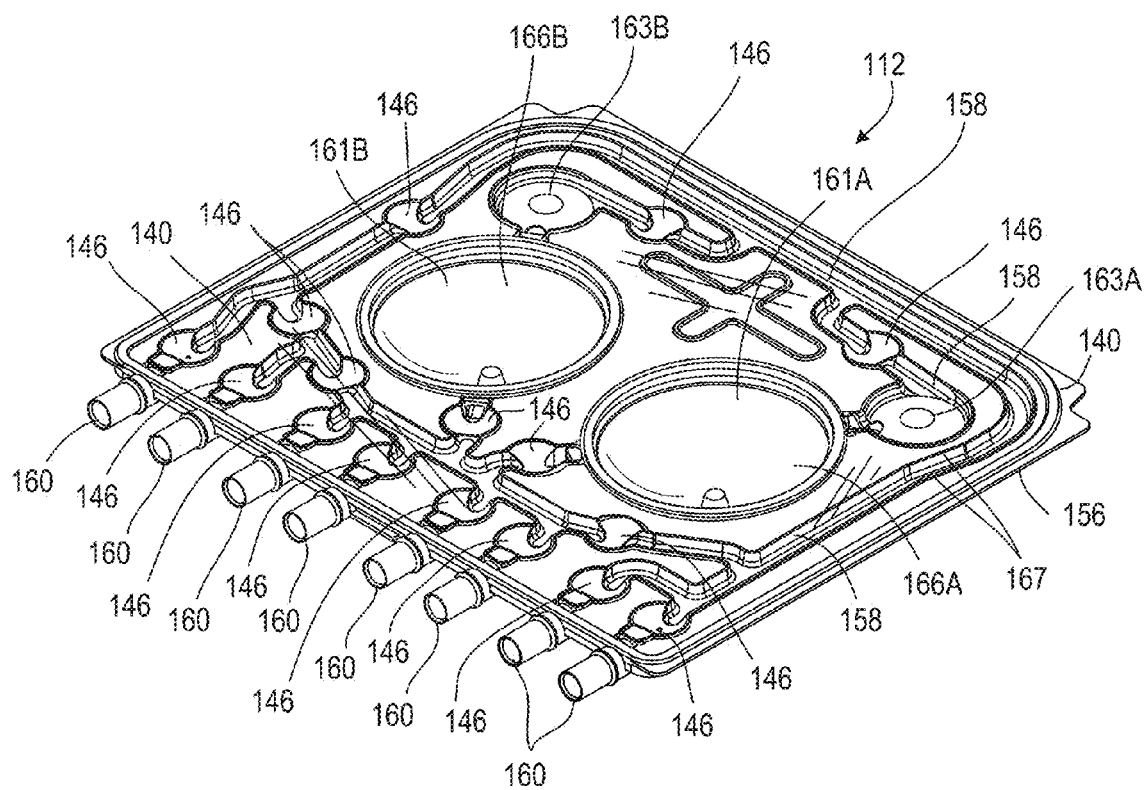
FIG. 6 is a perspective view of the fully assembled PD cassette of FIG. 4, from a flexible membrane and dome-shaped fastening member side of the PD cassette.
Figure 7:
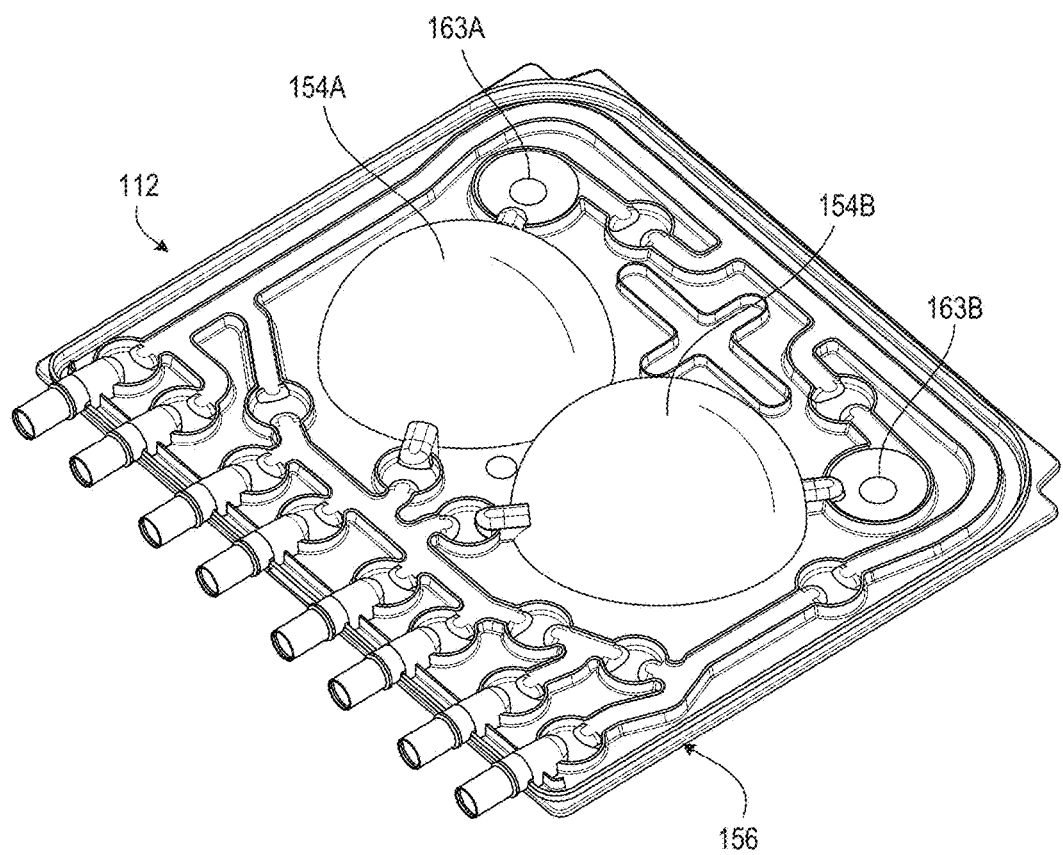
FIG. 7 is a perspective view of the fully assembled PD cassette of FIG. 4, from a rigid base side of the PD cassette.

FIG. 4 is an exploded, perspective view of the cassette 112, FIG. 5 is a perspective, cross-sectional view of the fully assembled cassette 112, and FIGS. 6 and 7 are perspective views of the assembled cassette 112, from the membrane side and from the rigid base side, respectively. Referring to FIGS. 4-6, the flexible membrane 140 of the cassette 112 is attached to a periphery of the tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102 of FIG. 3. In some implementations, the dome-shaped fastening members 161A, 161B have a diameter, measured from the outer edges of flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B, as shown in FIG. 5, form annular projections 168A, 168B that extend radially inward and annular projections 176A, 176B that extend radially outward from the side walls of the dome-shaped fastening members 161A, 161B. When the piston heads 134A, 134B (shown in FIG. 3) are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 134B. Because the membrane 140 is attached to the dome-shaped fastening members 161A, 161B, movement of the dome-shaped fastening members 161A, 161B into and out of the recessed regions 162A, 162B of the base 156 (e.g., due to reciprocating motion of the pistons 133A, 133B of FIG. 3) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Referring to FIGS. 4 and 6, raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable valve members 142 of the PD machine 102 act on the cassette 112 during use. During use, the dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of dialysate through the cassette 112 can be controlled through the selective depression of the depressible dome regions 146 by selectively inflating the inflatable members 142 of the PD machine 102.

Still referring to FIGS. 4 and 6, the fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. In some examples, the connectors 160 are bonded to tubing that is integral cassette 112. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette, as shown in FIGS. 1 and 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B, and vice versa.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some implementations, these components of the cassette 112 are formed of one or more polymers, such as polypropylene, polyvinyl chloride, polycarbonate, polysulfone, and other medical grade plastic materials. In some implementations, these components can be formed of one or more metals or alloys, such as stainless steel. These components of can alternatively be formed of various different combinations of the above-noted polymers and metals. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some implementations, the membrane 140 is about 100 micron to about 150 micron in thickness. However, various other thicknesses may be sufficient depending on the type of material used to form the membrane 140.

Figure 8:
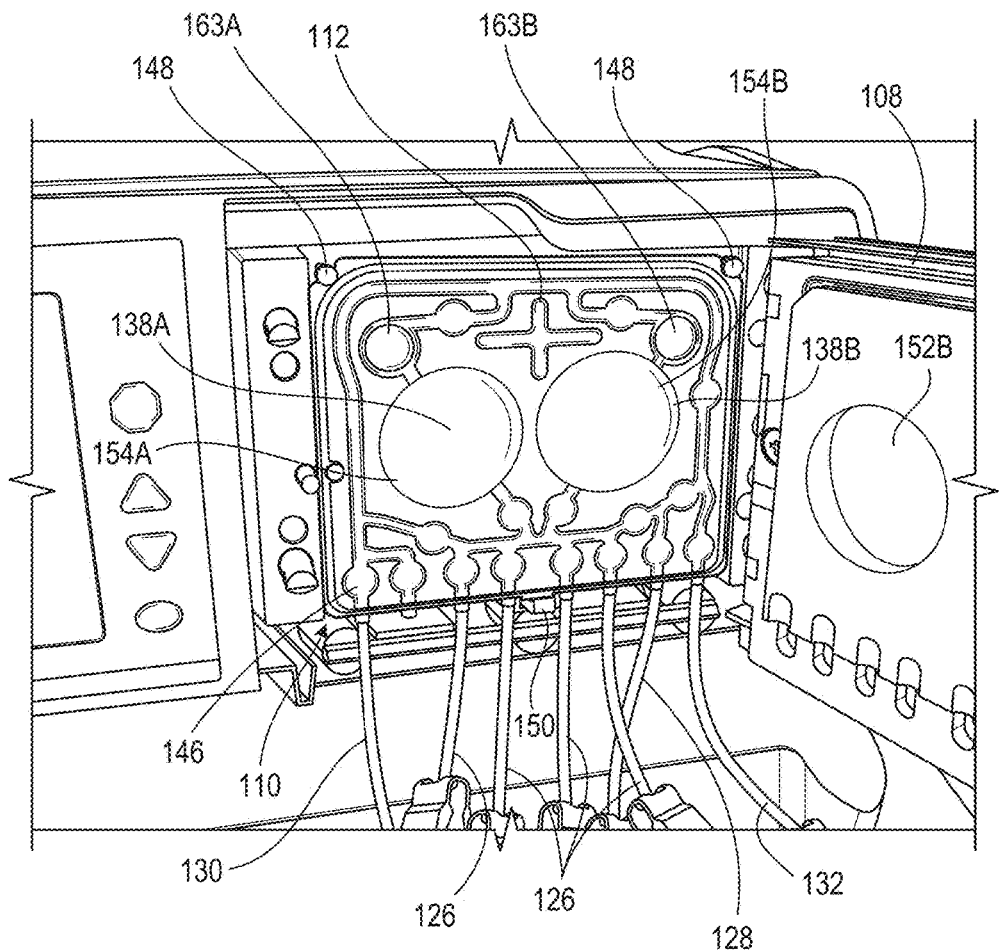
FIG. 8 is a perspective view of the PD cassette in the cassette compartment of the PD cycler of the PD system of FIG. 1.

As shown in FIG. 8, before treatment, the door 108 of the PD machine 102 is opened to expose the cassette interface 110, and the cassette 112 is positioned with its dome-shaped fastening members 161A, 161B aligned with the pistons 133A, 133B of the PD machine 102, its pressure sensing chambers 163A, 163B aligned with the pressure sensors 151A, 151B of the PD machine 102, its depressible dome regions 146 aligned with the inflatable members 142 of the PD machine 102, and its membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108. The pistons 133A, 133B are typically retracted into the piston access ports 136A, 136B during installation of the cassette 112 to avoid interference between pistons 133A, 133B and the dome-shaped fastening members 161A, 161B and thus increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. This compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146 (shown in FIG. 6). Referring briefly also to FIGS. 1 and 2, the patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to dome-shaped fastening members 161A, 161B of the cassette 112 to permit priming of the cassette 112 and the lines 126, 128, 130, 132. Once these components have been primed, treatment can be initiated.

FIGS. 9A-9G, which will be discussed below, are cross-sectional views of the system during different stages of the setup, priming, and treatment. These figures focus on the interaction between the piston 133A of the PD machine 102 and the pump chamber 138A of the cassette 112 during the setup, priming, and treatment. The interaction between the other piston 133B and pump chamber 138B is identical and thus will not be separately described in detail.

Figure 9A:
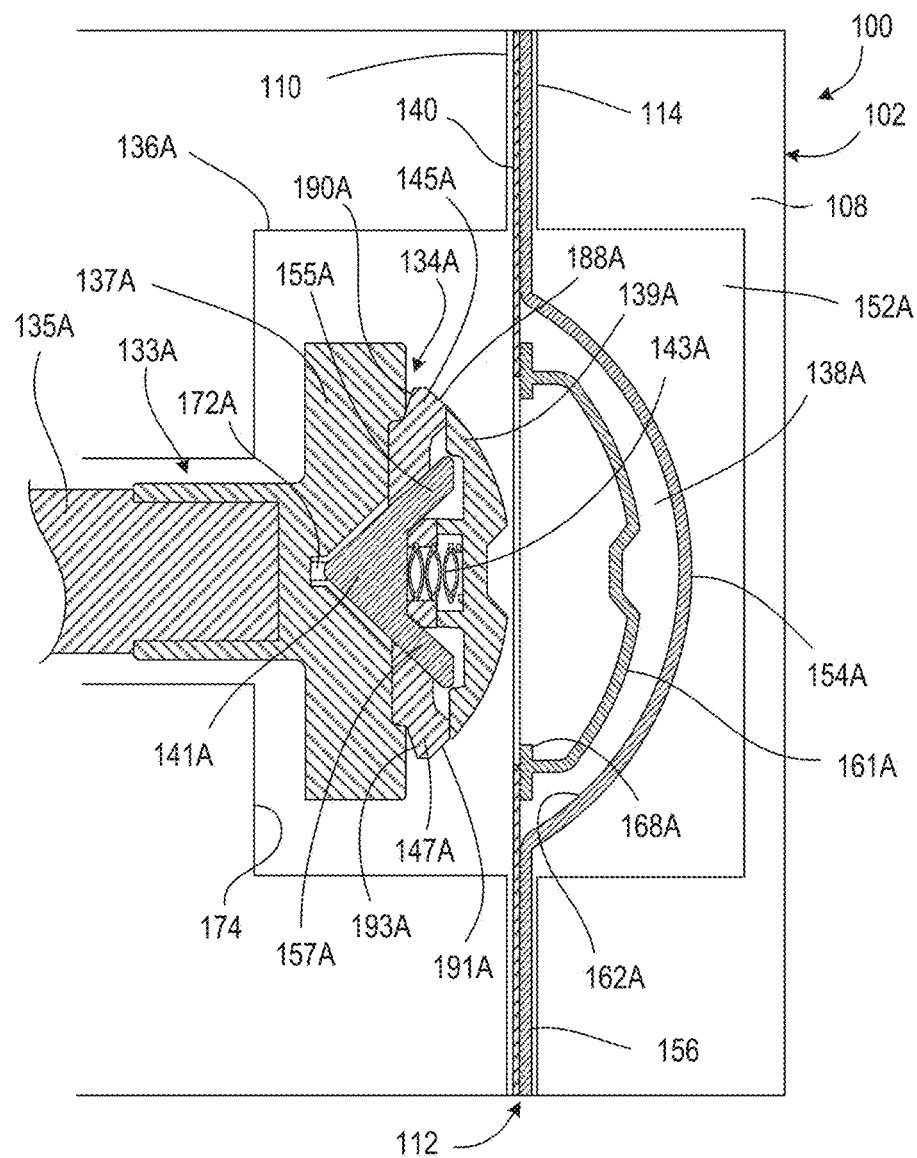
FIGS. 9A-9G are diagrammatic cross-sectional views of the PD system of FIG. 1 with the PD cassette disposed in the cassette compartment of the PD cycler, during different phases of a PD treatment and setup.

FIG. 9A shows the piston 133A fully retracted into the piston access port 136A of the cassette interface 110. The cassette 112 is positioned in the cassette compartment 114 of the PD machine 102 and the inflatable pad in the door 108 of the PD machine 102 is inflated such that the cassette 112 is pressed tightly against the cassette interface 110 of the PD machine 102, as explained above.

Figure 9B:
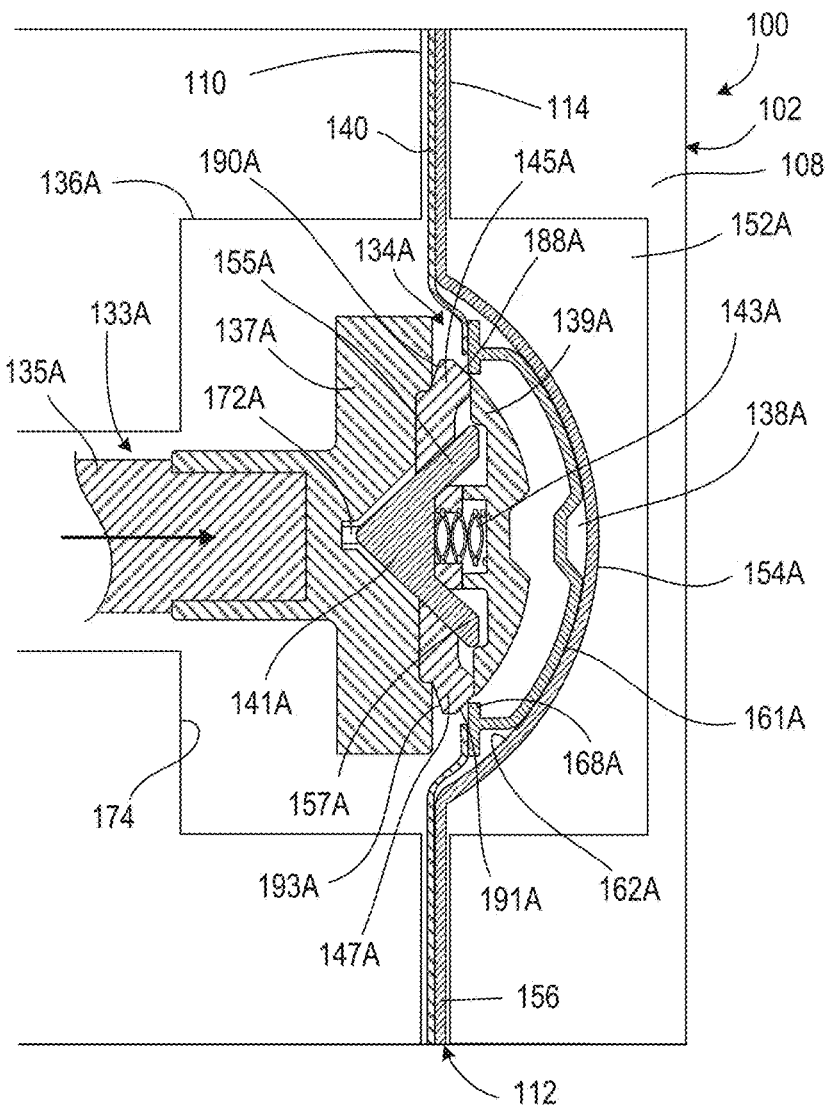

Referring to FIG. 9B, with the cassette 112 properly installed within the cassette compartment 114 of the PD machine 102 and the appropriate line connections made, the piston 133A is advanced to initiate the process of mechanically connecting the piston head 134A of the PD machine 102 to the dome-shaped fastening member 161A of the cassette 112. As the piston 133A is advanced, a front angled surface 188A of a sliding latch 145A and a front angled surface 191A of a sliding latch 147A contact a rear surface of the annular projection 168A, which extends radially inward from the dome-shaped fastening member 161A. The rear surface of the annular projection 168A is approximately perpendicular to the longitudinal axis of the piston 133A.

As the piston 133A continues to advance, the dome-shaped fastening member 161A contacts the inner surface of the portion of the rigid base 156 that forms the recessed region 162A, as shown in FIG. 9B. The rigid base 156 prevents further forward movement of the dome-shaped fastening member 161A. The membrane 140, which is attached to the peripheral flange 164A of the dome-shaped fastening member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped fastening member 161A, the sliding latches 145A, 147A are caused to move radially inward (i.e., toward the longitudinal axis of the piston 133A) as the piston head 134A continues to be advanced relative to the dome-shaped fastening member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped fastening member 161A. The radial inward movement of each of the sliding latches 145A, 147A in turn causes a forward movement of a latch lock 141A of the piston head 134A due to the mated geometries of the outer surfaces of legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by a spring 143A in the piston head.

Figure 9C:
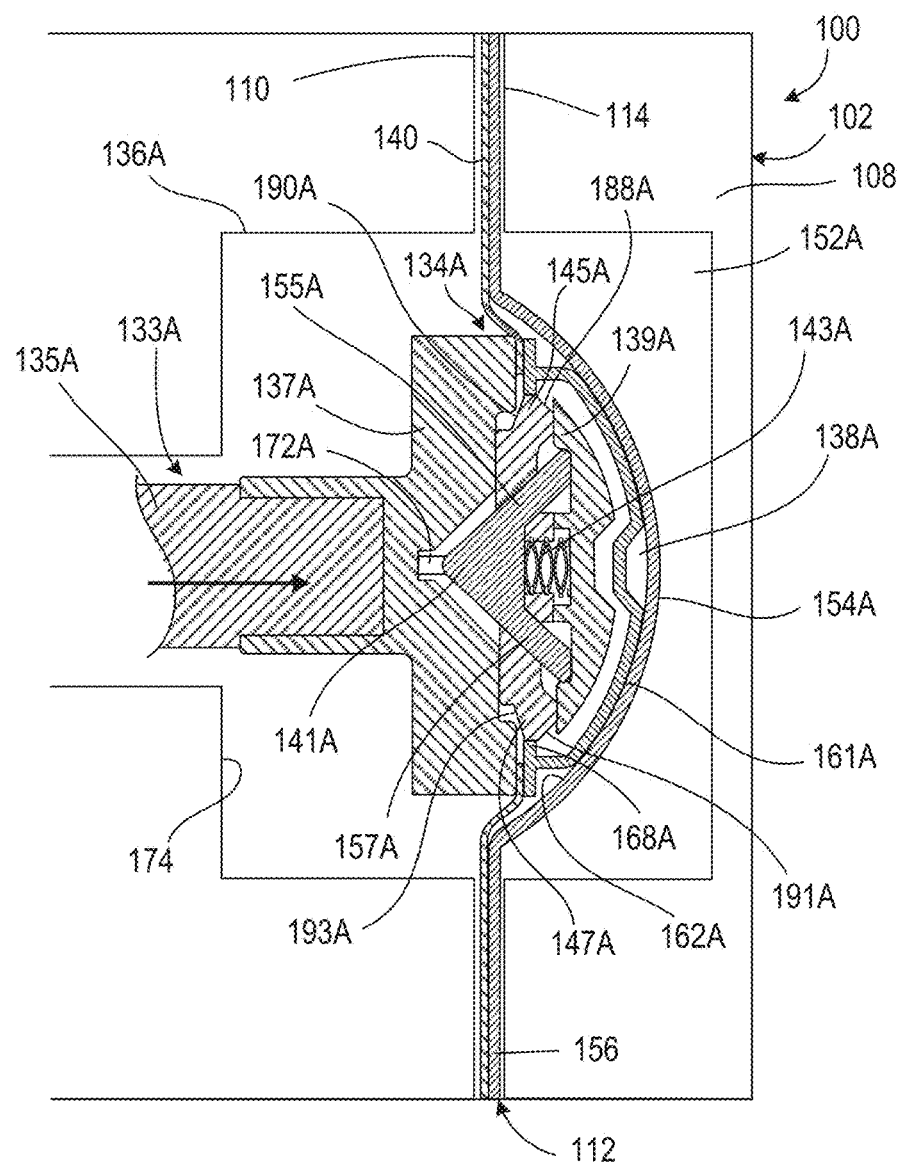

FIG. 9C shows the piston head 134A at a point during the connection process at which the sliding latches 145A, 147A have been deflected radially inward a sufficient distance to allow the sliding latches 145A, 147A to pass beyond the annular projection 168A that extends radially inward from the dome-shaped fastening member 161A. In this position, outer peripheral surfaces of the sliding latches 145A, 147A, which are substantially parallel to the longitudinal axis of the piston 133A, contact and slide along an inner surface of the annular projection 168A of the dome-shaped fastening member 161A, which is also substantially parallel to the longitudinal axis of the piston 133A. The spring 143A is further compressed due to the radially inwardly deflected positions of the sliding latches 145A, 147A.

Figure 9D:
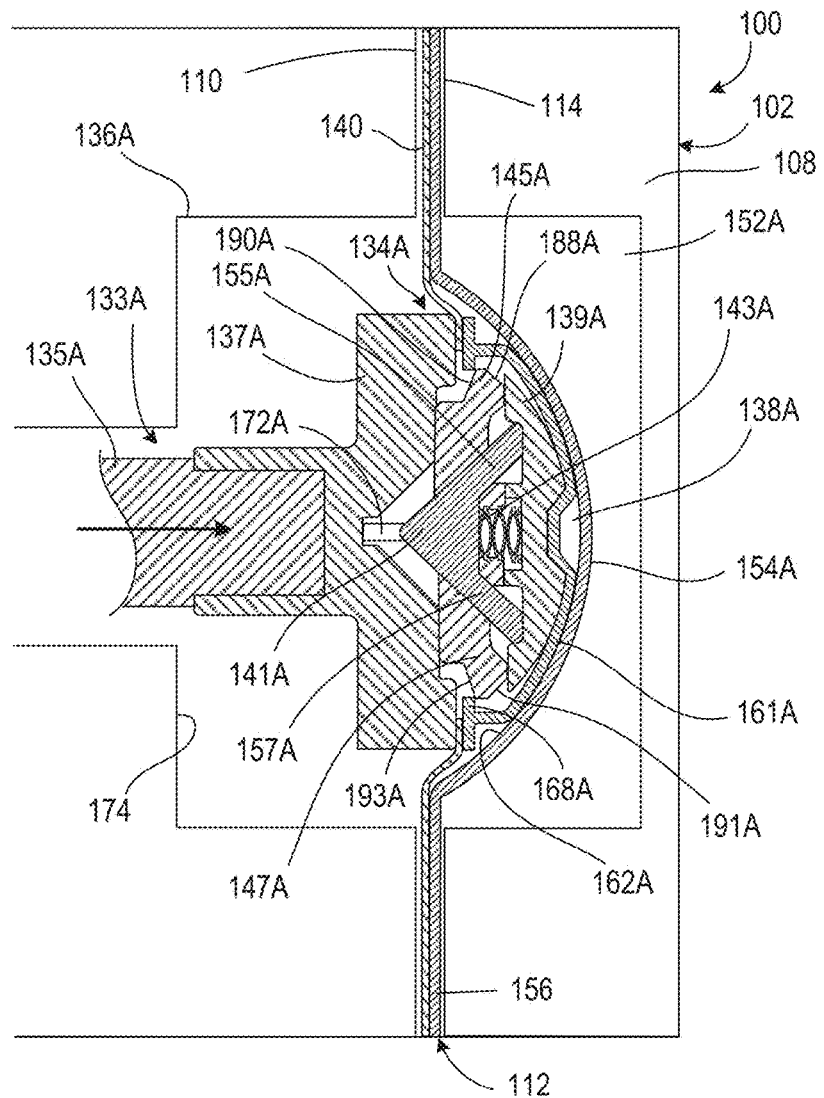

Referring to FIG. 9D, as the sliding latches 145A, 147A pass beyond the annular projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, causing the sliding latches 145A, 147A to move radially outward underneath the projection 168A of the dome-shaped fastening member 161A. Rear angled surfaces 190A, 193A of the sliding latches 145A, 147A ride along the front surface of the projection 168A of the dome-shaped fastening member 161A, which is slightly angled toward the rear of the dome-shaped fastening member 161A, as the sliding latches 145A, 147A move radially outward. The sliding latches 145A, 147A become wedged beneath the projection 168A as the sliding latches 145A, 147A move radially outward.

Figure 9E:
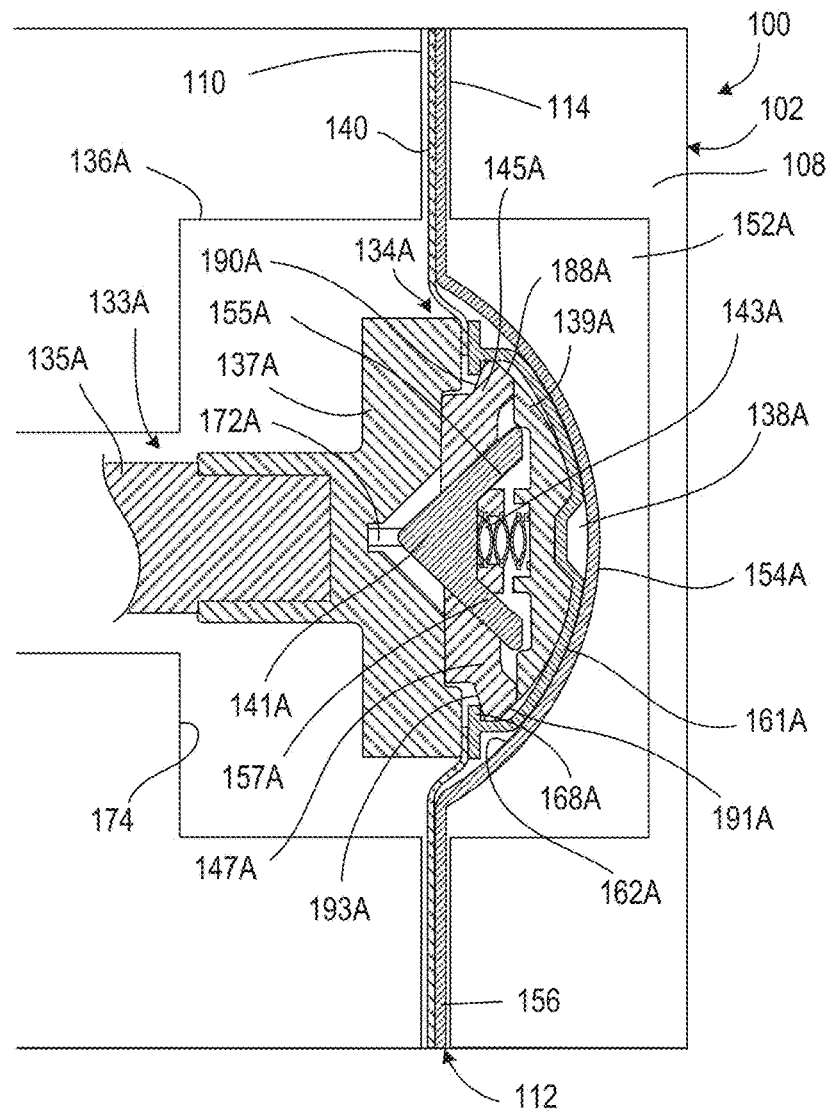

FIG. 9E illustrates the completed mechanical connection between the piston head 134A and the dome-shaped fastening member 161A in which the sliding latches 145A, 147A have moved to maximum outwardly displaced positions within the dome-shaped fastening member 161A. In this configuration, the projection 168A of the dome-shaped fastening member 161A is effectively pinched between a rear member 137A of the piston head 134A and the sliding latches 145A, 147A, resulting in a secure engagement between the piston head 134A and the dome-shaped fastening member 161A. As a result of the secure engagement of the piston head 134A to the dome-shaped fastening member 161A, the amount of slippage of the piston head 134A relative to the dome-shaped fastening member 161A can be reduced (e.g., minimized) and thus precise pumping can be achieved.

After mechanically coupling the piston head 134A of the PD machine 102 to the dome-shaped fastening member 161A of the cassette 112, a priming technique is carried out to remove air from the cassette 112 and from the various lines 126, 128, 130, 132 connected to the cassette 112. To prime the cassette 112 and the lines 126, 128, 130, 132, the piston 133A and inflatable members 142 are typically operated to pump dialysate from the heater bag 124 to the drain and from each of the dialysate bags 122 to the drain. Dialysate is also passed (e.g., by gravity) from the heater bag 124 to the patient line 130 to force any air trapped in the patient line out of a hydrophobic filter positioned at the distal end of the patient line 130.

Figure 9F:
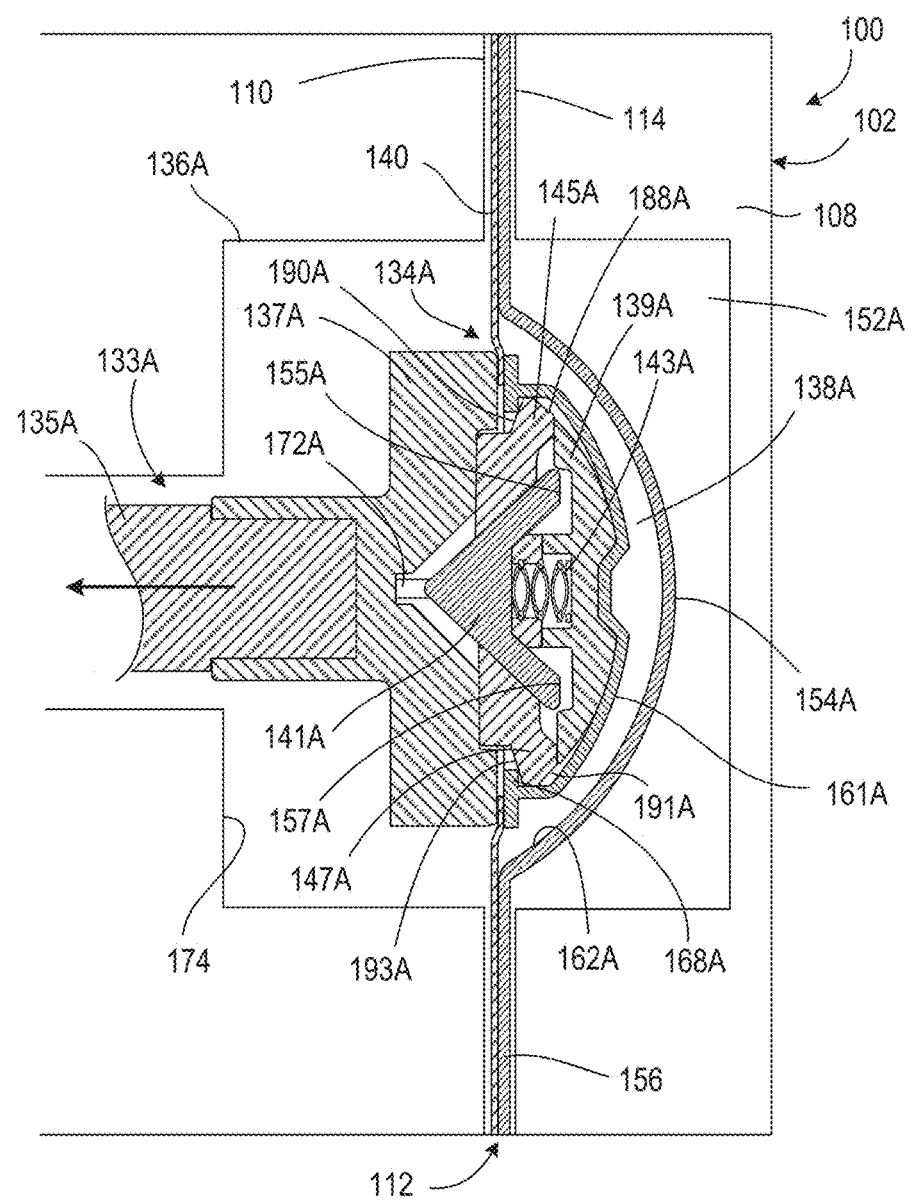

After priming is complete, the patient line 130 is connected to the patient and the PD machine 102 is operated to drain any spent dialysate that was left in the patient's peritoneal cavity from a previous treatment. To drain the spent dialysate from the patient's peritoneal cavity, the inflatable members 142 of the PD machine 102 are configured to create an open fluid flow path between the patient line 130 and the port 187A (shown in FIG. 4) of the pump chamber 138A, and the piston 133A is retracted to draw spent dialysate from the peritoneal cavity of the patient into the pump chamber 138A via the patient line 130, as shown in FIG. 9F. Because the piston head 134A is mechanically connected to the dome-shaped fastening member 161A and the dome-shaped fastening member 161A is attached to the membrane 140 of the cassette 112, the retraction of the piston 133A causes the dome-shaped fastening member 161A and the portion of the membrane 140 attached to the dome-shaped fastening member 161A to move rearwardly. As a result, the volume of the pump chamber 138A is increased and spent dialysate is drawn into the pump chamber 138A from the peritoneal cavity of the patient. The spent dialysate travels from the patient line 130 through the pressure sensing chamber 163A and then enters the pump chamber 138A via the port 187A. The pressure sensor 151A is able to monitor the pressure in the pressure sensing chamber 163A, which is approximately equal to the pressure in the pump chamber 138A, during this process.

Figure 9G:
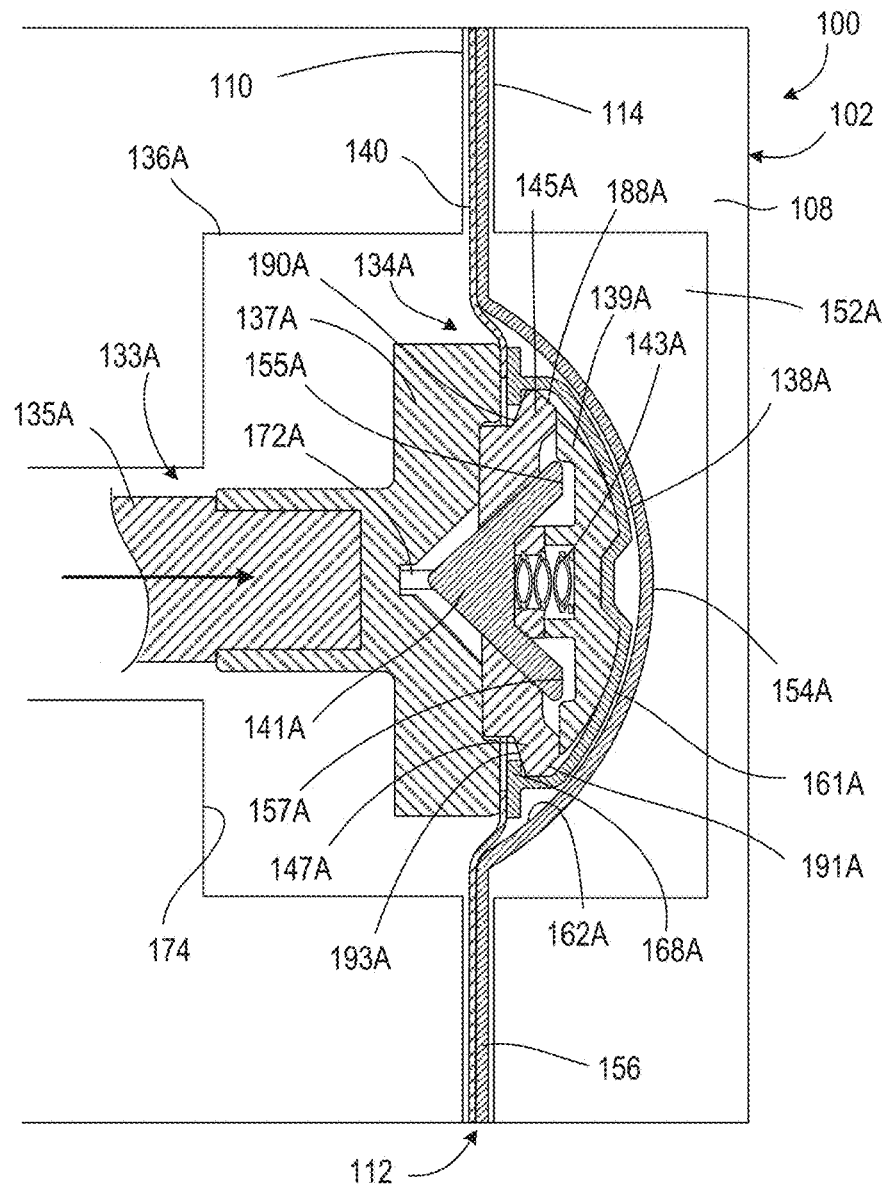

Referring to FIG. 9G, after drawing the dialysate into the pump chamber 138A from the peritoneal cavity of the patient, the inflatable members 142 are configured to create an open fluid flow path between the port 185A (shown in FIG. 4) of the pump chamber 138A and the drain line 132, and the dialysate is forced out of the pump chamber 138A to the drain by advancing the piston 133A and decreasing the volume of the pump chamber 138A. The piston 133A is typically advanced until the dome-shaped fastening member 161A contacts or nearly contacts the inner surface of the recessed region of the base 156 so that substantially all of the dialysate is forced out of the fluid pump chamber 138A via the port 185A.

During the patient drain phase of the treatment, the pistons 133A, 133B are typically alternately operated such that the piston 133A is retracted to draw spent dialysate solution into the pump chamber 138A from the patient while the piston 133B is advanced to pump spent dialysate solution from the pump chamber 138B to the drain and vice versa.

To begin the patient fill phase, the inflatable members 142 are configured to create a fluid flow path between the pump chamber 138A and the heater bag line 128, and then the piston 133A is retracted, as shown in FIG. 9F, to draw warm dialysate from the heater bag 124 to the pump chamber 138A. The warm dialysate travels from the heater bag 124 through the heater bag line 128 and into the pump chamber via the port 185A.

The warm dialysate is then delivered to the peritoneal cavity of the patient via the patient line 130 by configuring the inflatable members 142 to create a clear fluid flow path between the pump chamber 138A and the patient line 130 and advancing the piston 133A, as shown in FIG. 9G. The warm dialysate exits the pump chamber 138A via the port 187A and travels through the pressure sensing chamber 163A to the patient line 130 before reaching the peritoneal cavity of the patient. The pressure sensor 151A is able to monitor the pressure in the pressure sensing chamber 163A, which is approximately equal to the pressure in the pump chamber 138A, during this process.

During the patient fill phase of the treatment, the pistons 133A, 133B are typically alternately operated such that the piston 133A is retracted to draw warm dialysate into the pump chamber 138A from the heater bag 124 while the piston 133B is advanced to pump warm dialysate from the pump chamber 138B to the patient and vice versa. When the desired volume of dialysate has been pumped to the patient, the machine 102 transitions from the patient fill phase to a dwell phase during which the dialysate is allowed to sit within the peritoneal cavity of the patient for a long period of time.

During the dwell period, toxins cross the peritoneum of the patient into the dialysate from the patient's blood. As the dialysate dwells within the patient, the PD machine 102 prepares fresh dialysate for delivery to the patient in a subsequent cycle. In particular, the PD machine 102 pumps fresh dialysate from one of the four full dialysate bags 122 into the heater bag 124 for heating. To do this, the pump of the PD machine 102 is activated to cause the pistons 133A, 133B to reciprocate and certain inflatable members 142 of the PD machine 102 are inflated to cause the dialysate to be drawn into the fluid pump chambers 138A, 138B of the cassette 112 from the selected dialysate bag 122 via its associated line 126. The dialysate is then pumped from the fluid pump chambers 138A, 138B to the heater bag 124 via the heater bag line 128.

After the dialysate has dwelled within the patient for the desired period of time, the spent dialysate is pumped from the patient to the drain in the manner described above. The heated dialysate is then pumped from the heater bag 124 to the patient where it dwells for a desired period of time. These steps are repeated with the dialysate from two of the three remaining dialysate bags 122. The dialysate from the last dialysate bag 122 is typically delivered to the patient and left in the patient until the subsequent PD treatment.

After completion of the PD treatment, the pistons 133A, 133B are retracted in a manner to disconnect the piston heads 134A, 134B from the dome-shaped fastening members 161A, 161B of the cassette. The door 108 of the PD machine 102 is then opened and the cassette 112 is removed from the cassette compartment 114 and discarded.

FIG. 10 shows a schematic diagram of the PD machine 102 connected to a patient. The patient line 130 is connected to the patient's abdomen via the catheter 1002, and the catheter is connected to the patient line via the port 1004. The patient line 130 may be a tube made of a flexible material (e.g., a polymer) that is at least partially distended by operating pressures in the PD machine 102. For example, the patient line 130 may be an elastic polymer tube that develops a swell in response to positive operating pressures in the PD machine 102. The patient line 130, the port 1004, and the catheter 1002 are sometimes referred to herein as the patient line-catheter conduit, or simply the conduit. At least one of the pressure sensors 151A, 151B is located at a proximal end of the patient line 130 (e.g., at the end of the patient line 130 that is nearest to the PD machine 102). At least one of the pressure sensors 151A, 151B is selectably configured to measure the pressure in the patient line 130. In some implementations, the pressure sensors 151A, 151B include a transducer that generates a signal as a function of the pressure imposed. The signal is indicative of the magnitude and sign of the measured pressure.

During a PD treatment cycle, an occlusion can occur at different locations in the conduit. For example, the patient line 130 may become kinked or pinched, holes in the catheter 1002 may become occluded (e.g., with omental fat), or the patient line 130 may develop an internal blockage at some location (e.g., from a deposit of omental fat). The PD machine 102 is configured to adjust its operation in response to an occlusion being detected. For example, the control unit 139 may be configured to adjust one or more operating parameters of the PD machine 102 in an attempt to clear the occlusion and/or to modulate the flow in the patient line to avoid an overpressure condition. In some implementations, the control unit 139 may be configured to provide an alert indicating that an occlusion has been detected. For example, a visual, tactile, and/or audible alert may be directed to the patient (e.g., to wake the patient).

In order to determine an appropriate response, the PD machine 102 is configured to ascertain the type of occlusion that is present. In some implementations, the type of occlusion can be inferred based on the location of the occlusion in the conduit. For example, if an occlusion is detected in the catheter 1002, the PD machine 102 can infer that holes in the catheter 1002 may be occluded. Similarly, if the occlusion is detected somewhere along the patient line 130, the PD machine 102 can infer that the patient line 130 is kinked or pinched. The PD machine 102 is configured to determine a location of the occlusion relative to the position of the pressure sensor 151A, 151B. The particular location of the occlusion can be considered by the PD machine 102 to determine the appropriate response. In the example shown in FIG. 10, an occlusion 1008 is present in the patient line 130 at a distance x from the pressure sensor 151A (e.g., at or near the patient line inlet), which may be indicative of a kink or a pinch in the patient line 130.

Motion (e.g., rapid motion) of the pump mechanism creates an impulse (e.g., a step input and/or a near-instantaneous pulse) in local pressure. The onset or stoppage of flow of the PD solution (e.g., the dialysate) can present a wavefront. In response, the patient line 130 may develop a deformity. For example, the elastic material of the patient line 130 may locally expand (in the case of positive pressure) or locally contract (in the case of negative pressure) in response to the step input. The local (e.g., positive or negative) distension in cross-sectional area travels axially along the wall of the patient line 130 itself (e.g., as opposed to traveling in the PD solution) as an elastic wave. The wave carries with it local pressure variations, which may be detected by the pressure sensor 151A, 151B that is sampling fast enough to resolve the pulse as it travels.

When an elastic wave encounter a discontinuity in the dispersion relation of the elastic wave, at least a portion of the wave is reflected back toward the source. An occlusion in the conduit, or a kink or pinch in the line, are examples of such a discontinuity. Thus, when the elastic wave encounters the occlusion 1008, at least a portion is reflected back toward the pressure sensor 151A, 151B. The speed at which the elastic wave travels (e.g., the propagation speed) is the same in both directions, and is a function of the material properties and the geometry (e.g., cross-sectional geometry) of the materials comprising the conduit. The pressure sensor 151A, 151B is used to determine the timing of the wave's motion. For example, a single pulse can be detected as a difference in timing, and a period of an oscillatory wave can be measured.

If the propagation speed $c_o$ of the elastic wave is known, and the time required for the elastic wave to travel from the pressure sensor 151A, to the occlusion 1008, and back to the pressure sensor 151A T is known, the distance traveled by the elastic waves (e.g., from the pressure sensor 151A, to the occlusion 1008, and back to the pressure sensor 151A) can be determined. The distance traveled can be divided by two to determine the location of the occlusion 1008 in the conduit relative to the location of the pressure sensor 151A. That is, the distance x along the conduit from the location of the pressure sensor 151A to the location of the occlusion 1008 can be determined according to Equation 1:

$$x = \frac{T * c_o}{2} \quad (1)$$

where T is the transit time of the elastic waves, $c_o$ is the propagation speed of the elastic waves, and x is the distance along the conduit from the location of the pressure sensor 151A to the location of the occlusion 1008 for the first reflection of the wave. The wave reflections continue; the reflected wave is again reflected by the proximal end of the tube, the reflection travels back toward the occlusion, and is in turn reflected back. At each step, energy is lost, thereby resulting in an oscillation with a decaying amplitude.

The propagation speed $c_o$ of the elastic wave in distensible tubing carrying an incompressible fluid can be determined according to Equation 2:

$$c_o = \frac{A}{\rho}\sqrt{\frac{\partial P}{\partial A}} \qquad (2)$$

where A is the cross-sectional area of the lumen of the tubing, ρ is the density of the fluid, and P is the local transmural pressure. The value of the term $$\frac{\partial P}{\partial A}$$

comes from the stress-strain relationship of the tubing. Thus, this term is a function of the elastic modulus of the tubing material and of the tube's cross-sectional dimensions. Accordingly, Equation 2 confirms that the propagation speed $c_o$ is a function of the material properties of the tube, the dimensions of the tube, and the density of the fluid traveling through the tube.

As mentioned above, elastic waves can be reflected (or, e.g., scattered) when they reach a discontinuity in the carrying medium. In the case of the 1-dimensional waves of interest in this example, such a discontinuity may be represented by a change in the characteristic impedance $Z_o$ of the tubing. The characteristic impedance $Z_o$ for a harmonic forcing of pressure waves (e.g., at frequency ω) in such a tube, accounting for the effect of viscous damping, can be determined according to Equation 3:

$$Z_o = \frac{\rho c_o^2}{i\omega A_o}\lambda \qquad (3)$$

where $A_o$ is the luminal area at zero P, i represents the imaginary number $\sqrt{-1}$, and λ is given by Equation 4:

$$\lambda = \left[\frac{1}{\rho c_o^2}\left(-\rho\omega^2 + \frac{8\pi\mu i\omega}{A_o}\right)\right]^{1/2} \qquad (4)$$

where μ is the dynamic viscosity of the fluid. If a traveling wave reaches a boundary at distance x in the conduit with a terminal impedance $Z_T$, defined by Equation 5:

$$Z_T(x) \equiv \frac{P(x,t)}{Q(x,t)} \qquad (5)$$

where P(x,t) and Q(x,t) are the local instantaneous transmural pressure and volumetric flow rate, respectively, a fraction of the wave will be reflected if $Z_T \neq Z_o$. The fraction of the wave reflected may be embodied by the reflection coefficient Γ given by Equation 6:

$$\Gamma = \frac{Z_o - Z_T}{Z_o + Z_T} \qquad (6)$$

In short, for the systems and techniques described herein, Equations 1-6 establish that: i) a local deviation in either the available area for flow, or the effective distensibility of the tubing, causes at least a partial reflection of elastic waves propagated through the tubing; and ii) for tubing of uniform properties and cross-section, the outgoing and reflected elastic waves will transit the unaffected length of tubing at a common speed. Thus, if the transit time T of an elastic wave from the pressure sensor 151A, to the affected location (e.g., the location of the occlusion 1008), and back to the pressure sensor 151A is measured, and if the wave speed $c_o$ is known, the distance x along the conduit from the location of the pressure sensor 151A to the location of the occlusion 1008 can be determined according to Equation 1.

Because the outgoing and reflected elastic waves will transit the length of the tube at a common speed in a given system (e.g., because the propagation speed $c_o$ is a function of the material properties of the tube, the dimensions of the tube, and the density of the fluid traveling through the tube), the propagation speed $c_o$ may be initially determined for a given system (e.g., the dialysis system 100). Once the propagation speed $c_o$ is known, the transit time T of elastic waves can be measured. The distance x along the conduit from the location of the pressure sensor 151A to the location of the occlusion 1008 (e.g., the location of the occlusion) can then be determined.

In some implementations (e.g., implementations in which the conduit includes segments connected in series, such as a patient line and a catheter connected in series), the various segments of the conduit may have different elastic properties and/or cross-sectional dimensions. Further, the segments may be connected by fittings with yet other values of elastic properties and dimensions. While such complexities in the physical conduit carrying elastic waves may cause complexities in the characteristic relationship of transit time T versus distance x to the occlusion, this relationship may still be repeatable and monotonic, thus preserving the effectiveness of the method described herein.

Experiment 1

Figure 11:
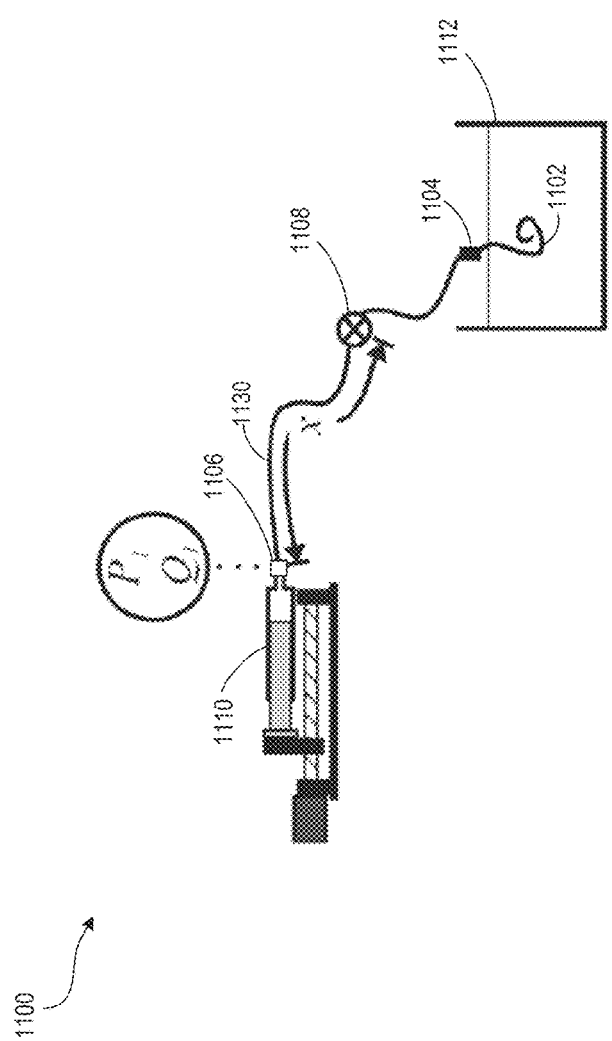
FIG. 11 shows an example experimental system for determining a propagation speed of elastic waves.

FIG. 11 shows an example experimental system 1100 in which the propagation speed $c_o$ of elastic waves can be determined. The system 1100 includes a syringe pump 1110 that is configured to produce flow into a conduit that includes a tube 1130 (e.g., which mimics a patient line) and a catheter 1102 connected to the tube 1130 via a port 1104. In this example, the syringe pump 1110 was driven by a programmable stepper motor. The catheter 1102 is submerged in a reservoir of fluid 1112 (e.g., in place of a patient). An occlusion 1108 is present in the tube 1130 at various distances x from a pressure sensor 306 that is positioned at a proximal end of the tube 1130. In this example, the occlusion was created by hemostat clamping the tube 1130 at various distances x. The clamping of the tube 1130 represents a complete occlusion.

A small volume (e.g., approximately 0.32 cubic centimeters) of water was injected by the syringe pump 1110 at a fixed rate (e.g., a relatively high rate of flow of 6.4 cubic centimeters per second). For example, the fixed rate of flow may create an impulse (e.g., a step input and/or a near-instantaneous pulse) in local pressure. At the end of the dispensing stroke, the flow of water was abruptly stopped. The tube 1130 develops a local distension in cross-sectional area due to the sudden injection of water that travels axially along the wall of the tube 1130 as an elastic wave. The elastic wave carries with it local pressure variations. As the elastic wave travels distally along the tube 1130, it reaches the occlusion 1108, and at least a portion is reflected back proximally toward the pump 1110.

The pressure sensor 1106 is configured to measure the pressure in the tube 1130 at the proximal end of the tube 1130 over time. The pressure measurements can be used to detect reflections of the elastic waves, in particular, times at which such reflections arrive at the proximal end of the tube 1130. In some implementations, the pressure measurements occur at a frequency in the order of ones of hertz, tens of hertz (e.g., 1-99 Hz), hundreds of hertz, or thousands of hertz (e.g., 1 kHz-2 kHz). The experiment is repeated at various distances x of the occlusion 1108.

FIGS. 12A-G show representative graphs of pressure P (in mbar) measured by the pressure sensor 1106 versus time (in seconds). The occlusions 1108 (e.g., the clamping of the tube 1130) occur at distances x of 80 cm, 100 cm, 140 cm, 180 cm, 220 cm, 260 cm, and 295 cm, respectively.

Figure 12A:
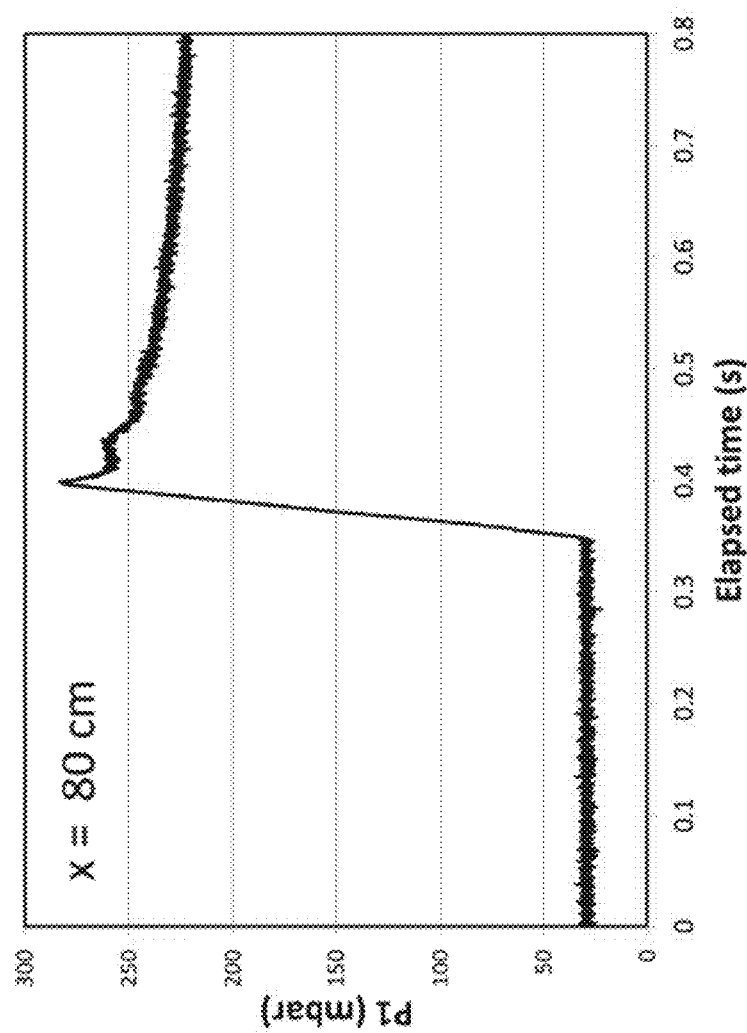
FIGS. 12A-G show representative graphs of pressures over time as measured by a pressure sensor of the system of FIG. 11.
Figure 12B:
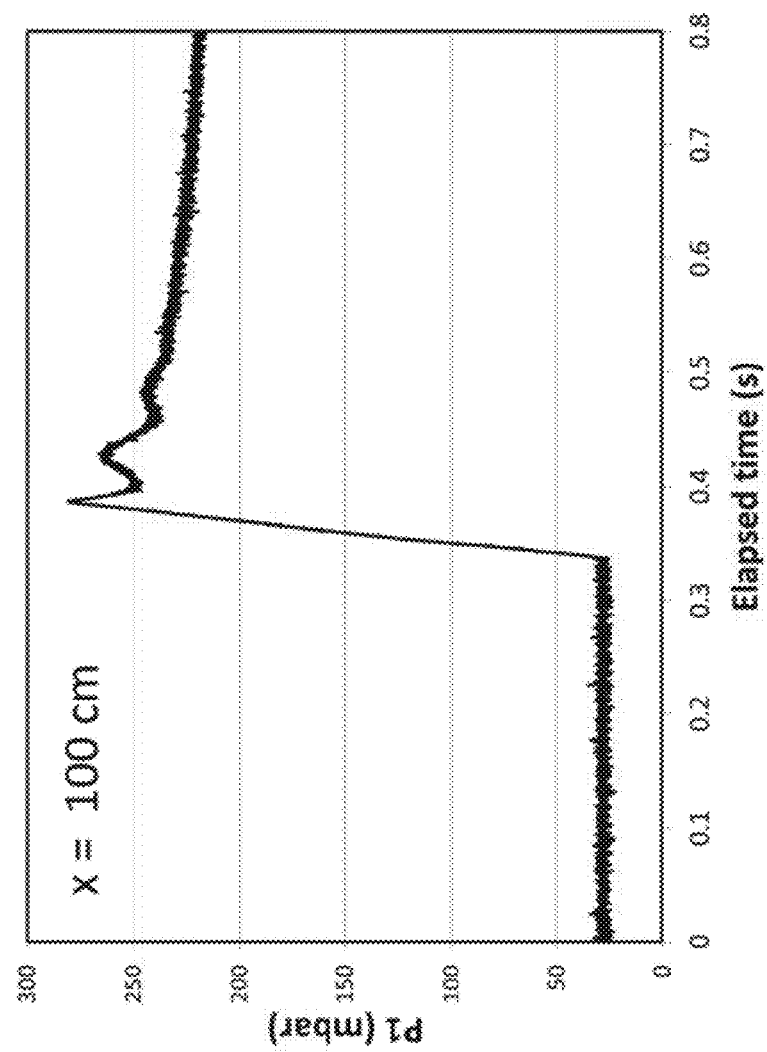
Figure 12C:
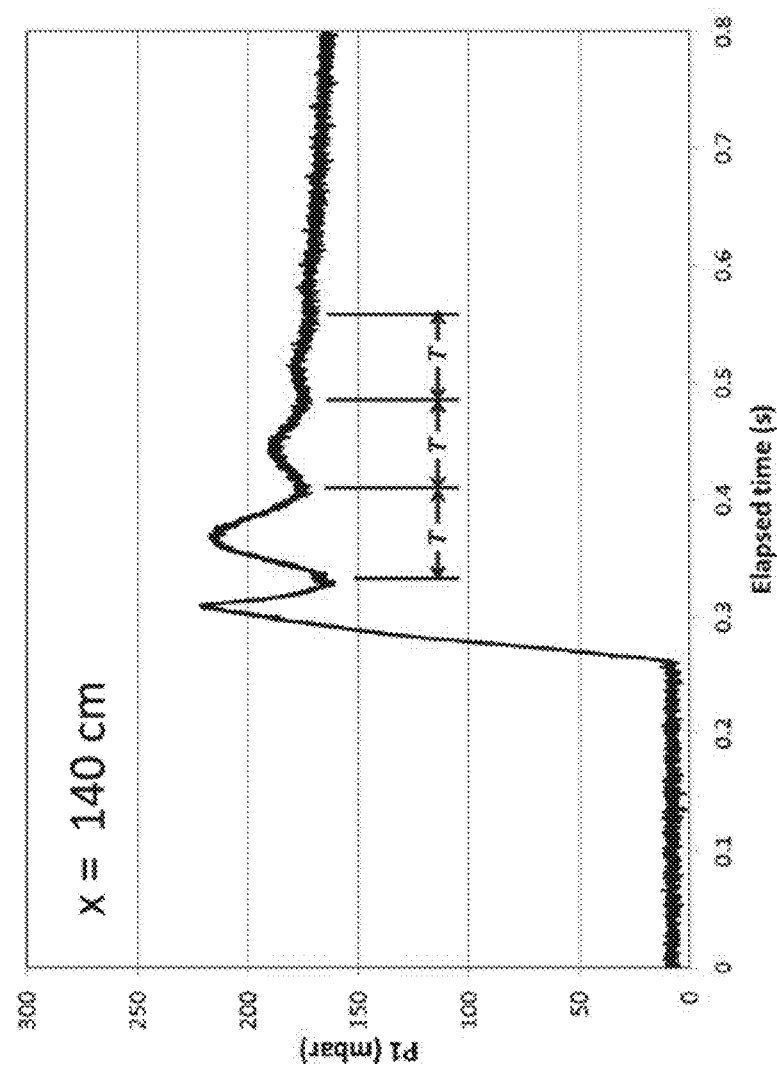
Figure 12D:
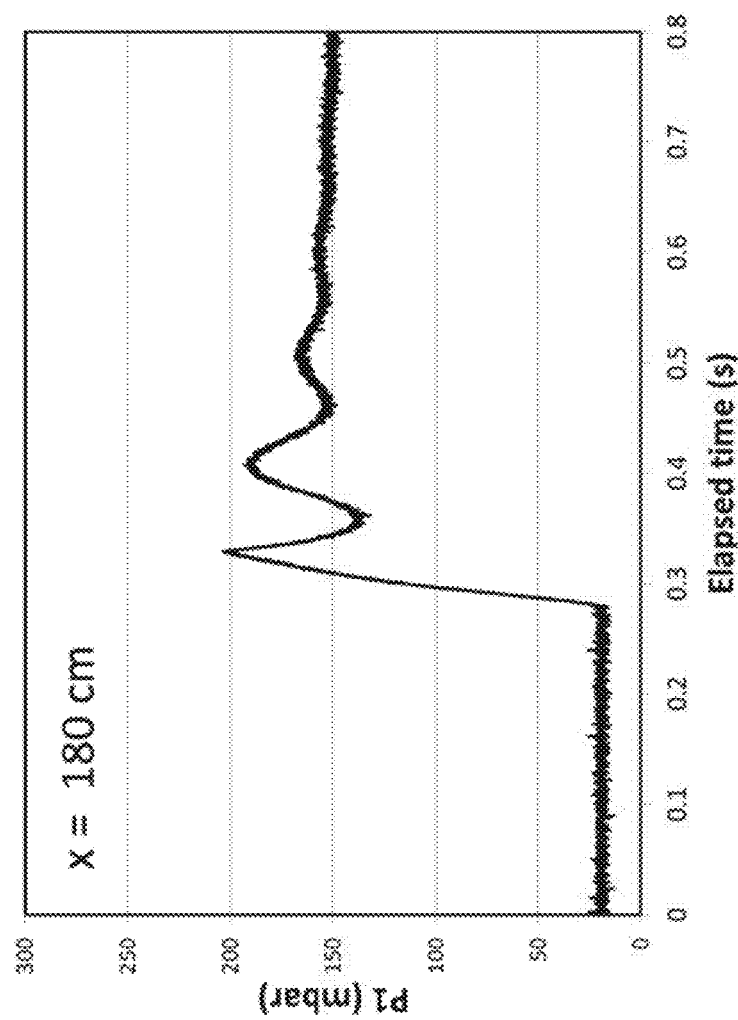
Figure 12E:
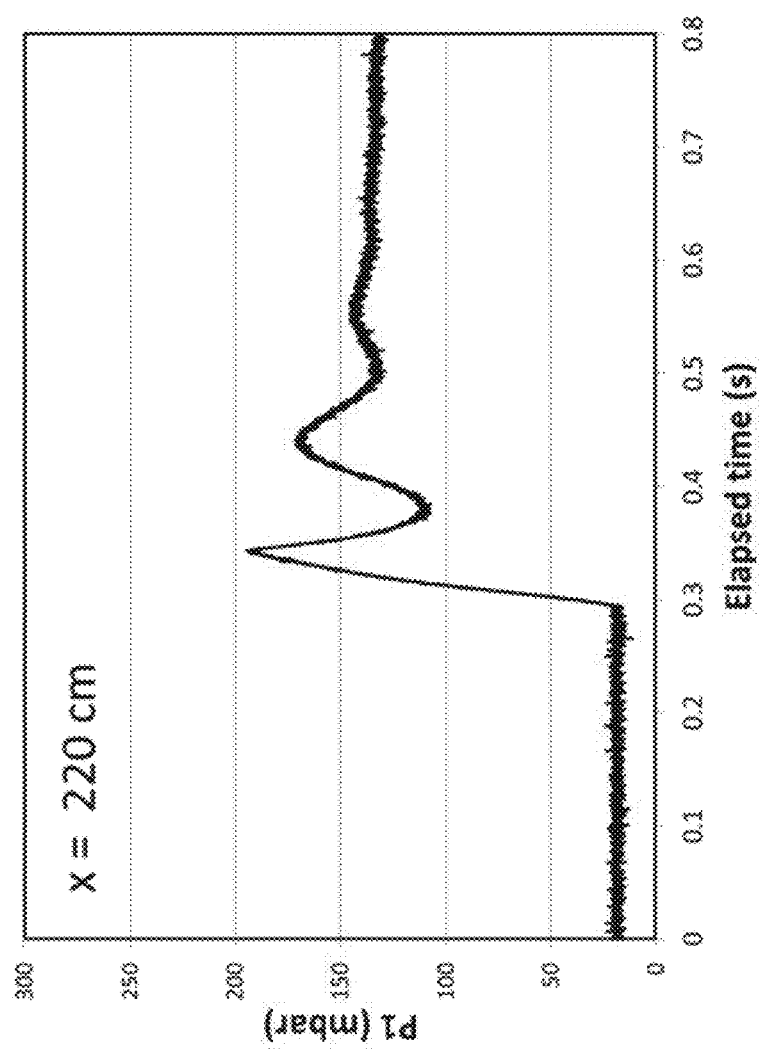
Figure 12F:
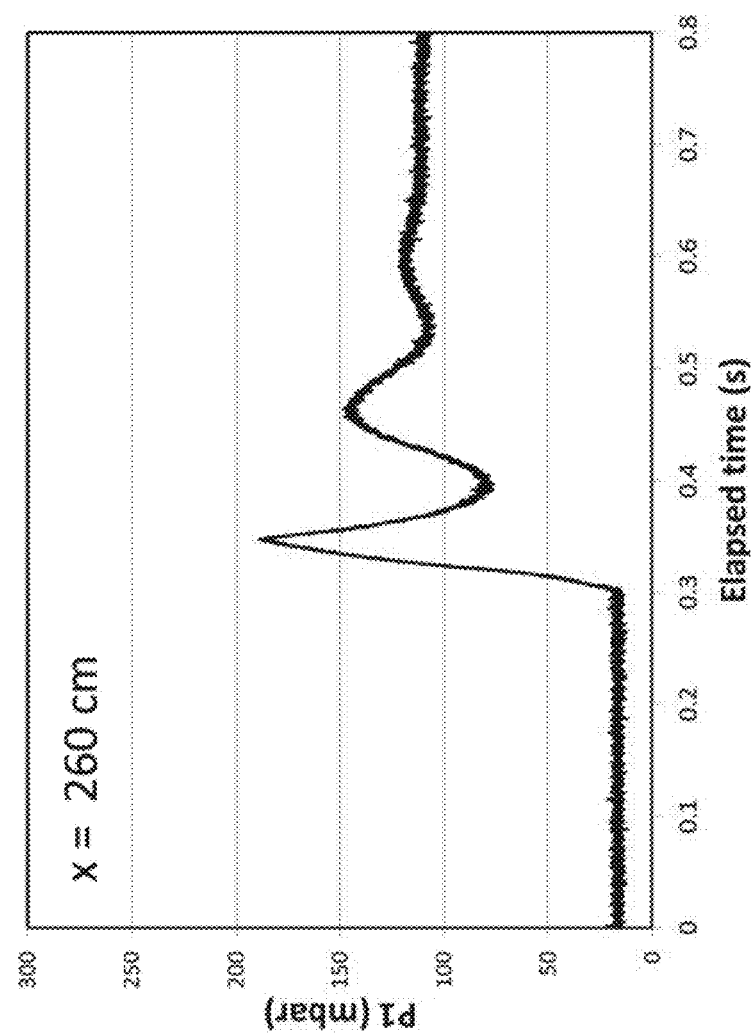
Figure 12G:
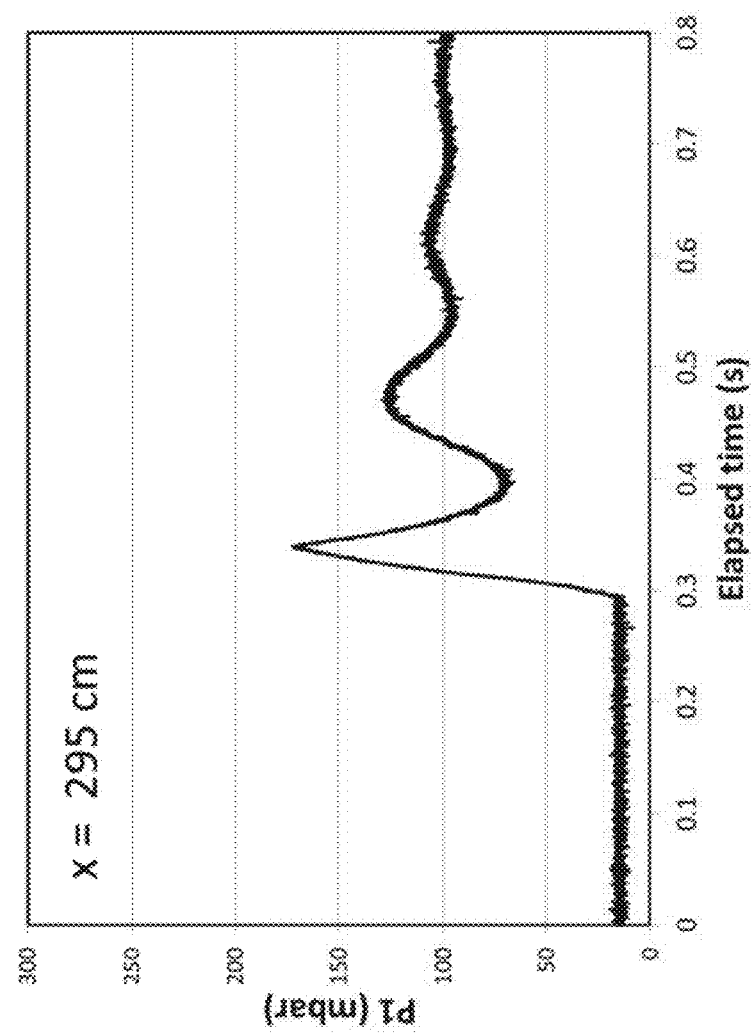

Referring to FIG. 12C, which shows pressures P measured when the tube 1130 was clamped at a distance x of 140 cm, the measured pressure is initially slightly above ambient and rises substantially uniformly during the pumping stroke. After the substantially uniform rise, oscillations occur. The period T of the oscillations (e.g., the transit time T of the elastic wave from the pressure sensor 1106, to the location of the occlusion 1108, and back to the pressure sensor 1106) is approximately 78 milliseconds. Using Equation 1, the propagation speed $c_o$ of the elastic waves is determined to be approximately 36 meters per second.

The calculation of the propagation speed $c_o$ with reference to FIG. 12C is made under the assumption that the oscillations are attributable to successive arrivals of a reflected elastic wave. Because the propagation speed $c_o$ should be uniform across various locations of the occlusion 1108 (e.g., in the case of uniform tubing), additional tests were performed at various distances to corroborate the validity of Equation 1 and confirm that the oscillations were attributable to successive arrivals of a reflected elastic wave. While FIGS. 12A-G show representative graphs of pressure versus time for clampings that were located at distances of 80 cm to 295 cm, pressures may be measured using other clamping locations. In some implementations, additional signal processing can be performed to extend limits of occlusion detection to any location of occlusions.

Figure 13:
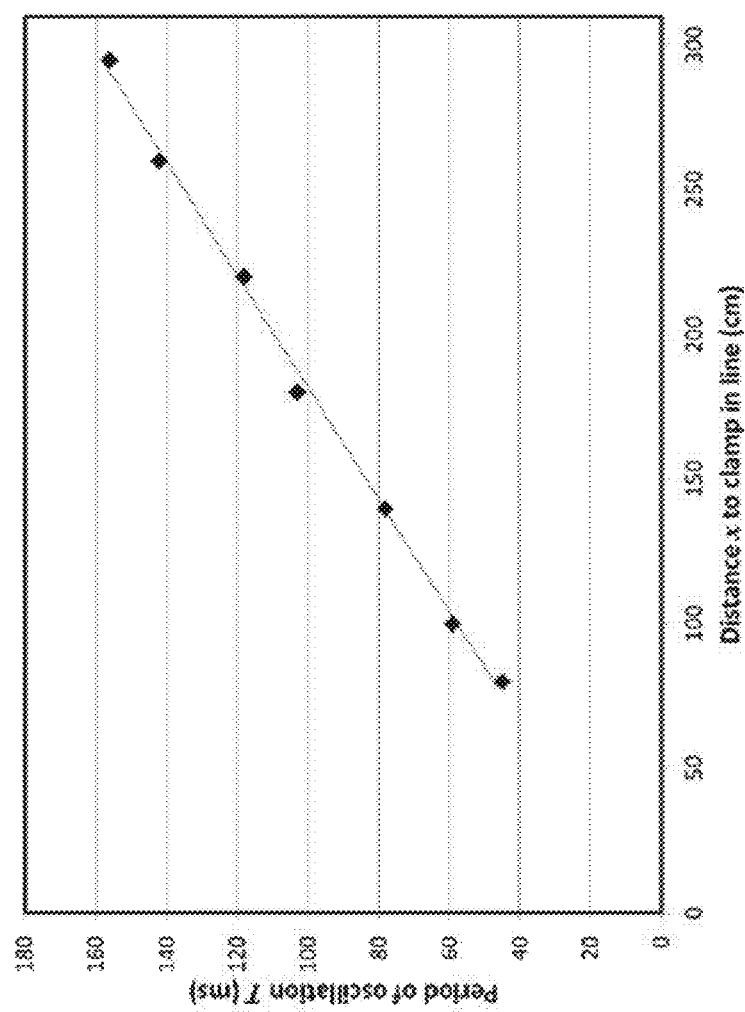
FIG. 13 shows a representative graph of oscillation periods versus various clamping distances measured using the experimental system of FIG. 11.

FIG. 13 shows a representative graph of the periods T of the oscillations (in milliseconds) versus the various distances x of the clamping locations (in centimeters). The measured periods T are based on the data shown in FIGS. 12A-G. The data shown in FIG. 13 indicates that the measured periods T (e.g., the transit time T of the elastic wave from the pressure sensor 1106, to the location of the occlusion 1108, and back to the pressure sensor 1106) are commensurate with the corresponding clamping distances x. That is, the data verify that the propagation speed $c_o$ of the elastic waves is substantially uniform (e.g., approximately 36±2 m/s) for all of the distances x measured, thereby corroborating the validity of Equation 1 and confirming that the oscillations are attributable to successive arrivals of reflected elastic waves. Now that the propagation speed $c_o$ is known, the transit time T of elastic waves can be measured to determine unknown distances x of other occlusions 1108 which may occur.

In some examples, the empirical determination of oscillation period T versus clamping distances x can be performed to characterize or "calibrate" the relationship between period T and distance x while accounting for non-uniform segments of the conduit. For example, the slope of the period T versus distance x curve of FIG. 13 may change at certain junctions in the conduit assembly, which in some examples can have the effects of enhancing the sensitivity of the detection method. In some examples, prior to treatment, an empirical determination can be made in which an occlusion is intentionally applied at known distances x, thereby providing a specific calibration of the current conduit assembly.

Experiment 2

While Experiment 1 corroborated the validity of Equation 1 in the experimental system 1100 of FIG. 11 testing for complete occlusions, Experiment 2 studies a similar technique implemented in an actual dialysis machine (e.g., the PD machine 102 of FIGS. 1-10) using the built-in pressure sensor 151A to test for partial occlusions. The advanced testing described below was performed to achieve results that are more relevant to real PD treatment.

The experiment primarily focused on flow in the drain direction. The choice to focus on flow in the drain direction was made for the following reasons: i) a majority of problematic blockages typically occur in the drain direction; ii) a greater potential for difficulty was predicted in the drain direction due to possible pull-off of cassette film from the pump; and iii) initial tests in the fill direction suggested that the same patterns of pressure versus flow should be obtainable—albeit with the potential for different calibration curves that may need to be empirically determined.

FIG. 14 shows a schematic of a dialysis system 1400 in which the propagation speed $c_o$ of elastic waves can be determined. The dialysis system 1400 includes the PD machine 102, the PD cassette 112 housed in the PD machine 102, a patient line 1430, and the pressure sensor 151A located at a proximal end of the patient line 1430. The patient line 1430 may be substantially similar to the patient line 130 described above with respect to FIGS. 1 and 10. In some implementations, the patient line 1430 may be a 10-foot patient line with dual patient connectors. In this example, the PD machine 102 is controlled by a computing device 1434 and a microcontroller 1436 such as an ATmega 2650 microcontroller manufactured by Atmel Corporation. In some implementations, the PD machine 102 may be controlled by a control unit (e.g., a processor) of the PD machine 102, such as the control unit 139 shown in FIG. 1. The microcontroller 1436 is operatively coupled to driver modules 1438*a*, 1438*b*. The driver modules 1438*a*, 1438*b* may be DRV8825 stepper motor driver modules manufactured by Pololu Corporation. The dialysis system 1400 includes various experimental components that can perform the functions of: i) introducing a controlled level of occlusion to the patient line 1430 at a known location; ii) enabling external programmable control of the pump heads to execute flow actuation according to the methods described herein; and iii) performing data acquisition from the onboard pressure sensor (e.g., the pressure sensor 151A) and in some examples a separate inline pressure sensor for validation purposes.

The microcontroller 1436, at the direction of commands issued by the computing device 1434, is configured to control the driver modules 1438*a*, 1438*b* to cause the driver modules 1438*a*, 1438*b* to operate pumps (e.g., the piston heads 134A, 134B) of the PD machine 102 in order to impose specified flow patterns. The microcontroller 1436 and the driver modules 1438*a*, 1438*b* provided pulse streams to the stepper motors driving the pumps to accomplish the following types of motion: i) return to the "home" position as defined by an onboard limit switch; ii) move forward at a specified step rate (e.g., to achieve a particular flow rate), by a specified number of steps, in a user-defined stepping mode from full stepping to various increments of microstepping; and iii) move backward at a specified step rate, by a specified number of steps in a user-defined stepping mode. Some flow patterns (e.g., characterized by combinations of step rates, number of steps, stepping mode, etc.) were determined to be more desirable than others for the purpose of occlusion detection. Such desirable flow patterns were programmed in a sequence that is described below.

The pumps are configured to cause fluid to be pumped through a patient line-catheter conduit that includes the patient line 1430, a catheter 1402, and a port 1404 that connects the patient line 1430 to the catheter 1402. The catheter 1402 may be a Flex Neck Classic catheter. The catheter 1402, the port 1404, and a portion of the patient line 1430 is submerged in a basin of water 1412 (e.g., in place of a patient). The water was held at room temperature (e.g., 20-25° C.). The free surface of the water was kept at the same height (e.g., ±1 centimeters) with respect to the direction of gravity as that of the pressure sensor 151A of the PD cycler 102. An occlusion 1408 was provided in the patient line 1430 at various distances x from the pressure sensor 151A. In this example, the occlusion 1408 was created using various methods and at various distances x, as described in more detail below. The occlusions 1408 represented both full and partial occlusions.

The experiment included the following general steps:
i. create an impulsive change in a pressure condition at the proximal end of the patient line 1430 (e.g., at the location of the pressure sensor 151A) by providing a short burst of water flow in either the fill or the drain direction that is abruptly ceased, thereby creating elastic waves in the patient line 1430;
ii. detect and measure the transit time T for elastic waves to travel from the pressure sensor 151A, to the location of the occlusion 1408, and back to the pressure sensor 151A; and
iii. empirically determine a calibration curve between the transit time T and the distance to the occlusion x, thereby determining an effective value of the propagation speed $c_o$ of the elastic waves.

The experiment was performed across a large number of cassettes, with different types, degrees, and locations of flow restriction (e.g., occlusions), in order to investigate the potential sensitivity (e.g., true positive rate) and specificity (e.g., true negative rate) of the detection method, as described in more detail below.

A small volume (e.g., approximately 0.33 cubic centimeters) of water was moved through the patient line 1430 in the drain direction by a first pump of the PD machine 102 (e.g., a pump controlled by a first one of the driver modules 1438a) at a fixed rate (e.g., 4.4 cubic centimeters per second). At the end of the stroke, the first pump was abruptly stopped. The patient line 1430 develops a local deformity due to the injected water. Such a deformity causes elastic waves to be generated in the patient line 1430. The pressure sensor 151A, which is built into the PD machine 102 and located at the proximal end of the patient line 1430, was used to detect the reflected elastic waves in a manner substantially similar to that described above with respect to FIG. 11.

The partial occlusions 1408 used in the experiment were characterized for their relative flow restrictions. The characterization was done quantitatively via the fluidic resistance $R_f$ values of the partial occlusions 1408 as given by Equation 7:

$$R_f = \frac{|\Delta P|}{Q} \quad (7)$$

where $\Delta P$=pressure difference from upstream to downstream of occlusion (8)

and $Q$=volumetric flow rate (9)

The pressures were initially measured using both the pressure sensor 151A of the PD machine 102 and a reference pressure transducer 1440 positioned downstream from the pressure sensor 151A. The separate pressure measurements were taken to ensure that the pressure sensor 151A built into the PD machine 102 was capable of achieving the sensitivity required to detect the elastic waves. For example, the pressure sensor 151A is configured to detect the pressure in the patient line 1430 through a membrane of the cassette 112, and various fluidic elements are positioned between the pressure sensor 151A and the proximal end of the patient line 1430. It was considered that these elements may have the potential to diminish and/or distort the elastic waves. Thus, measurements made by the reference pressure transducer 1440 were used to verify the fidelity of the measurements made by the pressure sensor 151A. A high degree of fidelity was observed, and the reference pressure transducer 1440 was removed to avoid possible artifacts.

Utilizing only measurements from the pressure sensor 151A of the PD machine 102, $\Delta P$ due to the applied occlusion 1408 was inferred by first obtaining a baseline pressure measurement with no occlusion 1408. The baseline pressure measurement was then subtracted from the pressure measurement with the occlusion 1408 according to Equation 10:

$$\Delta P = P_{with\ occlusion} - P_{without\ occlusion} \quad (10)$$

Due to the likelihood of turbulent flow and other sources of viscous pressure losses that are not linearly related to Q, the fluidic resistance $R_f$ for a given flow restriction is in general a function of Q. In order to isolate the effect of flow resistance from capacitive or inertial effects, $\Delta P$ is measured at steady state. For these reasons, measurements related to the fluidic resistance $R_f$ were performed under prolonged flow at a fixed flow value (e.g., a fixed flow value of Q=30 milliliters per minute). Such a flow value was chosen because it represents the critical value for the Drain Complication condition, described in more detail below, and is representative of the order of magnitude of mean flow rate occurring throughout a treatment.

The ability to detect a partial occlusion (e.g., as compared to detecting a complete occlusion) presents challenges that do not manifest when detecting a complete occlusion. Typically, the less restrictive an occlusion is, the greater is the challenge for sensitivity and specificity of a method for determining its location. A relevant standard for quantifying partial occlusions in the PD machine 102 comes from the Drain Complication and Fill Complication conditions. Drain Complication and Fill Complication conditions occur when there is a flow restriction sufficient to depress the flow below a threshold value for a particular period of time. In a model case of a steady-state flow restriction, the threshold value of restriction that would generate a Drain Complication is one that would require a pressure of approximately −200 mbar (as measured at the pressure sensor 151A) to drive a flow of approximately 30 milliliters per minute. Thus, the measurements related to the fluidic resistance $R_f$ were performed under prolonged flow at the fixed flow rate of Q=30 milliliters per minute. An occlusion that requires −200 mbar to produce a steady-state flow rate of 30 ml/min is referred to herein as a "drain-critical occlusion."

Applying Equation 7 to the conditions defined by the "drain-critical occlusion," the total fluidic resistance of the system 1400 can be determined according to Equation 11:

$$R_f^{drain-critical,total} = \frac{200 \text{ mbar}}{30 \text{ ml/min}} = 6.7 \frac{\text{mbar}}{\text{ml/min}} \quad (11)$$

In Equation 11, the superscript "total" refers to the fact that the pressure sensor 151A shows the effect of all fluidic resistances occurring in, and inherent to, the cassette 112, the patient line 1430, and the catheter 1402. Thus, some components of the total fluidic resistance are due to normally occurring elements in the flowpath (e.g., the conduit), $R_f^{baseline}$. Because such normally occurring elements are arranged in series with the additional resistance created by the occlusion 608, and due to the additive property of resistances in series, a drain-critical value of occlusion-specific resistance $R_f^{drain-critical.occlusion}$ can be determined according to Equation 12:

$$R_f^{drain-critical,occlusion} = R_f^{drain-critical,total} - R_f^{normal} \quad (12)$$

$R_f^{baseline}$ for patient line 1430, the port 1404 with two patient connectors, and the catheter 1402 was measured to be approximately 0.095 mbar/(ml/min). Thus, the drain-critical value of the fluidic resistance of a partial occlusion itself is approximately 6.7 mbar/(ml/min). Over the course of Experiment 2, partial occlusions 1408 were tested with occlusion-specific resistances in the range of approximately 1-10 mbar/(ml/min), thus representing values in the range of approximately 0.15-1.5 times the drain-critical value of occlusion-specific resistance $R_f^{drain-critical.occlusion}$.

The partial occlusions 1408 were designed to model two basic types of real occlusions: i) internal occlusions (e.g., in which an obstruction lodges itself within the lumen of the patient line 1430; and ii) external occlusions, in which the patient line 1430 is pinched from the outside. In designing the physical means of applying the partial occlusions 1408 to the patient line 1430 and/or the catheter 1402, the goal was to determine whether the detection method can provide a measurement of the distance x of the occlusion 1408 that is sensitive and specific for the distance x but insensitive to the type of restriction or the value of the fluidic resistance $R_f$ of the occlusion 1408 (e.g., for fluidic resistance $R_f$ values within the range of interest of approximately 1-10 mbar/(ml/min)).

Partial occlusions 608 of both types (e.g., internal and external) having repeatable fluidic resistance $R_f$ values were applied at various locations x over a relatively large number of cases to test for repeatability.

FIG. 15 shows a cross-sectional view of an example partial internal occlusion 1502 installed in the patient line 1430. The partial internal occlusion 1502 was fabricated to serve as a model of an internal occlusion. For example, the partial internal occlusion 1502 is meant to represent a partially blocked patient line, with a well-controlled orifice of known flow characteristics. The partial occlusion 1408 of FIG. 14 may represent the partial internal occlusion 1502. In this example, the internal occlusion 1502 is a cylindrical insert made of stainless steel, although other shapes and/or materials may be used. The internal occlusion 1502 is configured to be positioned at a chosen distance x such that the internal occlusion 1502 is sufficiently gripped by the patient line 1430 in order to remain in position throughout the tests. The internal occlusion 1502 includes a circular orifice 1504 for allowing the fluid tested (e.g., water) to flow through the internal occlusion 1502. The orifice 1504 has a diameter that results in the internal occlusion 1502 having a fluidic resistance $R_f$ value in the range of 1-10 mbar/(ml/min). The diameter of the orifice 1504 may result in particular fluidic resistance $R_f$ values for the occlusion 1502 according to Table 1:

| Diameter of orifice (mm) | $R_f$ mbar/(ml/min) |
|---|---|
| 0.30 | 8.7-9.1 |
| 0.34 | 5.5-6.4 |
| 0.38 | 3.1-3.2 |
| 0.51 | 0.8-1.0 |

The fluidic resistance $R_f$ values of the occlusion 1502 as shown in Table 1 depend on the particular working fluid used in the system 1400 (e.g., in this example, water). Thus, if a different fluid were used, such as dialysate, the fluidic resistance $R_f$ values would be different. The diameter or the orifice 1504 may be configured to have a diameter that results in appropriate fluidic resistance $R_f$ values based on the working fluid that is used. In this example, the diameters of the orifice 1504 were chosen to achieve the desired fluidic similarity with known conditions of interest for dialysate flow, using the drain-critical value $R_f$ as a benchmark as discussed above. Thus, the results presented herein are largely sufficient to validate the method for its applicability to the condition of dialysate as the working fluid. However, at least two characteristics would be expected to vary to some extent if dialysate were substituted for water as used in these tests. For example, the exact value of the propagation speed $c_o$ of the elastic waves is affected by the density of the fluid according to Equation 2. Further, the diameter of occlusion required to achieve a particular value of fluidic resistance is a function of fluid viscosity.

Figure 16A:
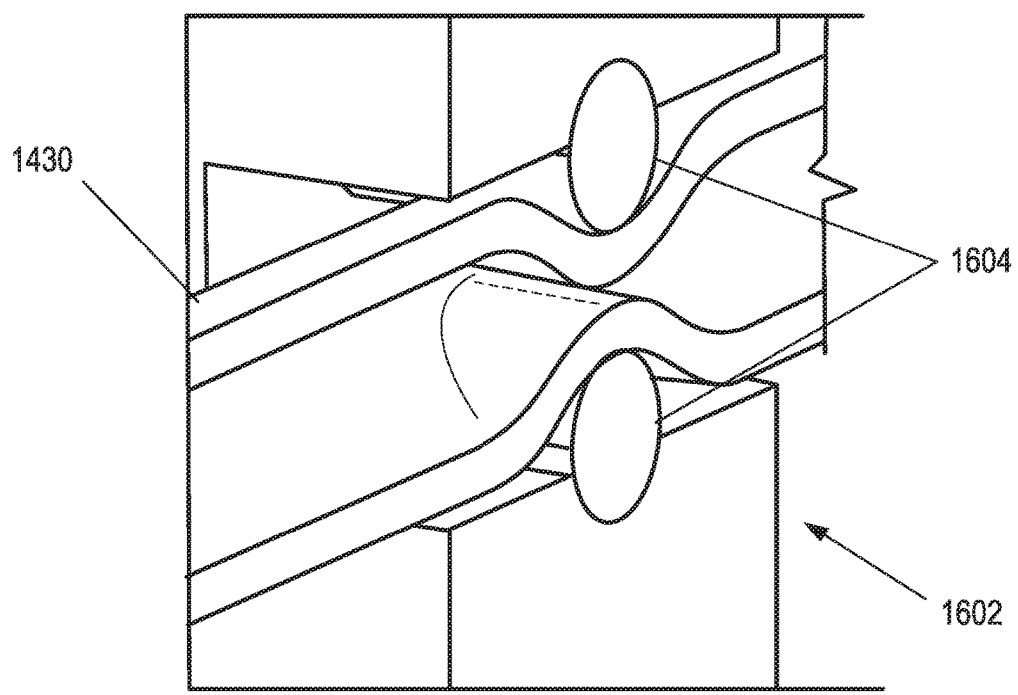
FIGS. 16A-B show a cutaway view and a photograph, respectively, of an example partial external occlusion.
Figure 16B:
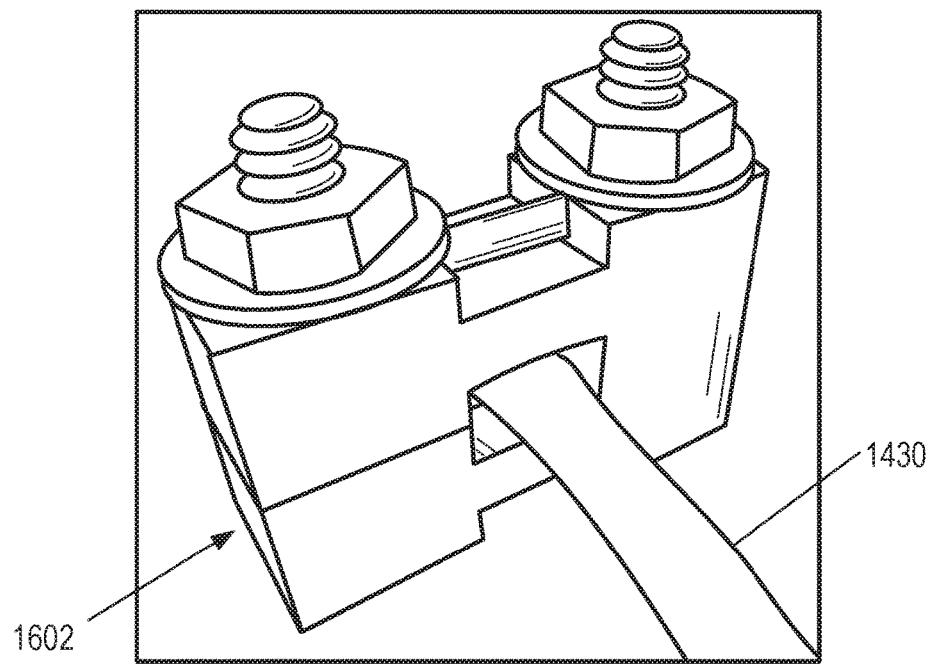

FIGS. 16A and 16B show a cutaway view and a photograph, respectively, of an example partial external occlusion applied to the patient line 1430. The partial external occlusion was fabricated to serve as a model of an external "pinching" style of occlusion. For example, the partial external occlusion is meant to represent the style of occlusion occurring when the patient line 1430 is pinched or kinked, with the applied value of restriction being precisely controlled during the test. The partial occlusion 1408 of FIG. 14 may represent the partial external occlusion 1502. In this example, the external occlusion is in the form of a clamping mechanism 1602 that is configured to apply a partial occlusion of the pinching type. The clamping mechanism 1602 includes rods 1604 that are configured to apply uniform stresses to substantially opposite surfaces of the patient line 1430 that cause the patient line 1430 to deform. In this example, the rods 1604 are made of stainless steel and have a diameter of 3.2 millimeters, although other dimensions and/or materials may be used. The stress applied to the patient line 1430 may be referred to as a Hertzian line-contact stress. The clamping mechanism 1602 also includes washers (e.g., Belleville washers) that are configured to cause the rods 1604 to press together as the clamping mechanism 1602 is tightened. For example, an operator may tighten the clamping mechanism 1602 during a "long-stroke" (e.g., having a flow value of approximately 30 milliliters per minute) to achieve a target pressure reading by the pressure sensor 151A, thereby actively setting the fluidic resistance $R_f$ value of the external occlusion desired for the particular test.

Referring again to FIG. 14, prior to any sequence of tests concerning a particular cassette 112, locations on the patient line 1430 were measured with a precision of approximately ±3 millimeters. The patient line 1430 and the catheter 1402 were then primed with water to substantially eliminate the presence of air bubbles in the conduit. The partial occlusion 1408 was then placed such that the occlusion 1408 was centered at the desired distance x. The testing was repeated for partial occlusions 1408 of both the internal and external type and having various fluidic resistance $R_f$ values.

For partial occlusions 1408 of the internal type (e.g., such as the partial internal occlusion 1502 of FIG. 15), the occlusion 1408 was first positioned near a distal end of the patient line 1430 (e.g., at a distance of approximately x=295 centimeters). The occlusion 1408 was then repositioned to various distances x for subsequent tests. Similar tests were also performed with the occlusion 1408 positioned in the catheter 1402. The patient line 1430 was primed after each repositioning of the occlusion 1408 to minimize the occurrence of air bubbles. For partial occlusions 1408 of the external type (e.g., such as the partial external occlusion in the form of a clamping mechanism 1602 of FIGS. 16A and 16B), the occlusion 1408 was positioned to the various distances x for testing. The patient line 1430 was primed after each repositioning of the occlusion 1408 to minimize the occurrence of air bubbles.

With the occlusion 1408 in place, both a "long-stroke" test for measuring the fluidic resistance $R_f$ of the occlusion 1408 and a "short-stroke" test (e.g., a sudden injection of approximately 0.32 cubic centimeters of fluid at a fixed flow rate of approximately 6.4 cubic centimeters per second) for determining the location of the blockage (e.g., the distance x) were performed.

The long-stroke test included a single, prolonged motion of the pump at a constant speed corresponding to a flow rate of Q=30 milliliters per minute. As described above, the pump is operated by the microcontroller 1436 and the driver modules 1438a, 1438b. The pressure sensor 151A was monitored during the test. The pressures measured by the pressure sensor 151A typically approached a steady-state value from the mid- to end-point of the stroke. The steady-state value was recorded for the purpose of calculating the fluidic resistance $R_f$.

The short-stroke test included one or more single rapid motions of the pump that were designed to impart a pressure impulse on the patient line 1430, thereby causing an elastic wave to be generated in the patient line 1430 as described above. The short-stroke test was performed by moving water having a volume of approximately 0.33 cubic centimeters through the patient line 1430, although other volumes could be used to optimize signal-to-noise ratio or the operational limitations of the dialysis system 1400. For a particular value of dispensed volume, the speed of the pump was maximized under appropriate constraints in order to maximize the amplitude of the pressure waveforms associated with the transit of the elastic waves. The constraints included avoidance of missed motor steps (e.g., momentary stalling of the motor by requiring power beyond its capability), avoidance of pressures outside the range of the pressure sensor 151A, and avoidance of damage to components of the dialysis system 1400.

Regarding avoidance of missed motor steps, preliminary tests were conducted with full-stepping of the pump stepper motor with pulse delays of 2.00, 2.50, and 3.00 milliseconds. Steps were occasionally missed for the 2.00 and 2.50 millisecond pulse delays, but were not missed for the 3.00 millisecond pulse delays. Thus, full-stepping of the pump motor with a total pulse delay of 3.00 milliseconds for 25 steps was employed, which resulted in a dispensed volume of 0.33 cubic centimeters. Pressures outside the range of the pressure sensor 151A and damage to components of the dialysis system 1400 were not observed to occur when operating at any of the pulse delays.

Figure 17A:
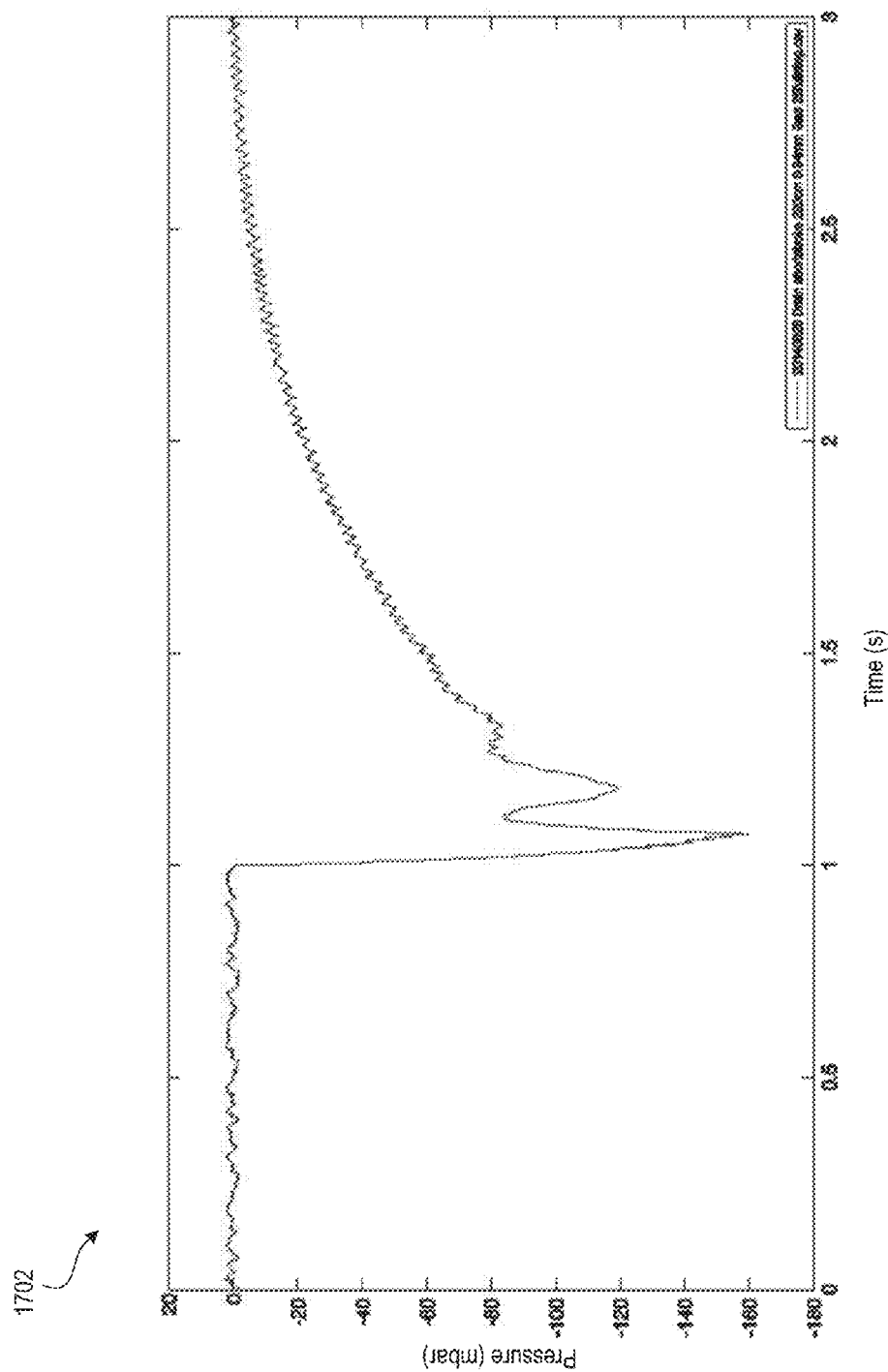
FIG. 17A shows a pressure waveform that includes pressure measurements over time made by a pressure sensor of the PD machine of FIG. 14.

FIG. 17A shows a pressure waveform 1702 that includes pressure measurements over time made by the pressure sensor 151A during the short-stroke test. The pressure measurements were sampled at a frequency of 1 kHz. In this example, the occlusion 1408 was positioned at a distance x=220 centimeters along the patient line 1430. The pump stroke had a duration of approximately 75 milliseconds. The measured pressure, steady in the absence of pump motion, is seen to drop rapidly during a pump stroke having a duration of approximately 75 milliseconds that commences at approximately t=1 second. After abrupt cessation of pump motion, oscillations occur due to the elastic effects described above. The period T of the oscillations (e.g., which corresponds to the transit time T of the elastic waves from the pressure sensor 151A, to the location of the occlusion 1408, and back to the pressure sensor 151A) can be evaluated to determine the propagation speed $c_o$ of the elastic waves according to Equation 1. Once the propagation speed $c_o$ of the elastic waves is known, locations x of occlusions (e.g., at unknown positions of the conduit) can subsequently be determined by evaluating the period T of oscillations.

Superimposed with the oscillations is high-frequency noise and a gradual decay from the peak excursion of pressure (e.g., at approximately t=1.075 seconds) toward zero. The decay occurs due to the occlusion 1408 being a partial occlusion. Because the high-frequency noise and the decay are not relevant for purposes of determining the period T of the oscillations, they can be removed from the waveform 1702 using one or more signal processing techniques. For example, the waveform 1702 can be smoothed to reduce the effect of the high-frequency noise using a moving average taken as the mean of the measured pressures spanning 15 milliseconds on either side of a given data point (e.g., sometimes referred to as a 15 millisecond half-width moving average). Further, a background curve approximating the overall decay onto which the oscillations are superimposed can be subtracted from the waveform 1702. The background curve to be subtracted from the waveform 1702 may be obtained, for example, using a 50 millisecond half-width moving average. Prior to applying the moving averages, the data were truncated to the time domain which begins at the cessation of the pump motion at approximately t=1.075 seconds.

Figure 17B:
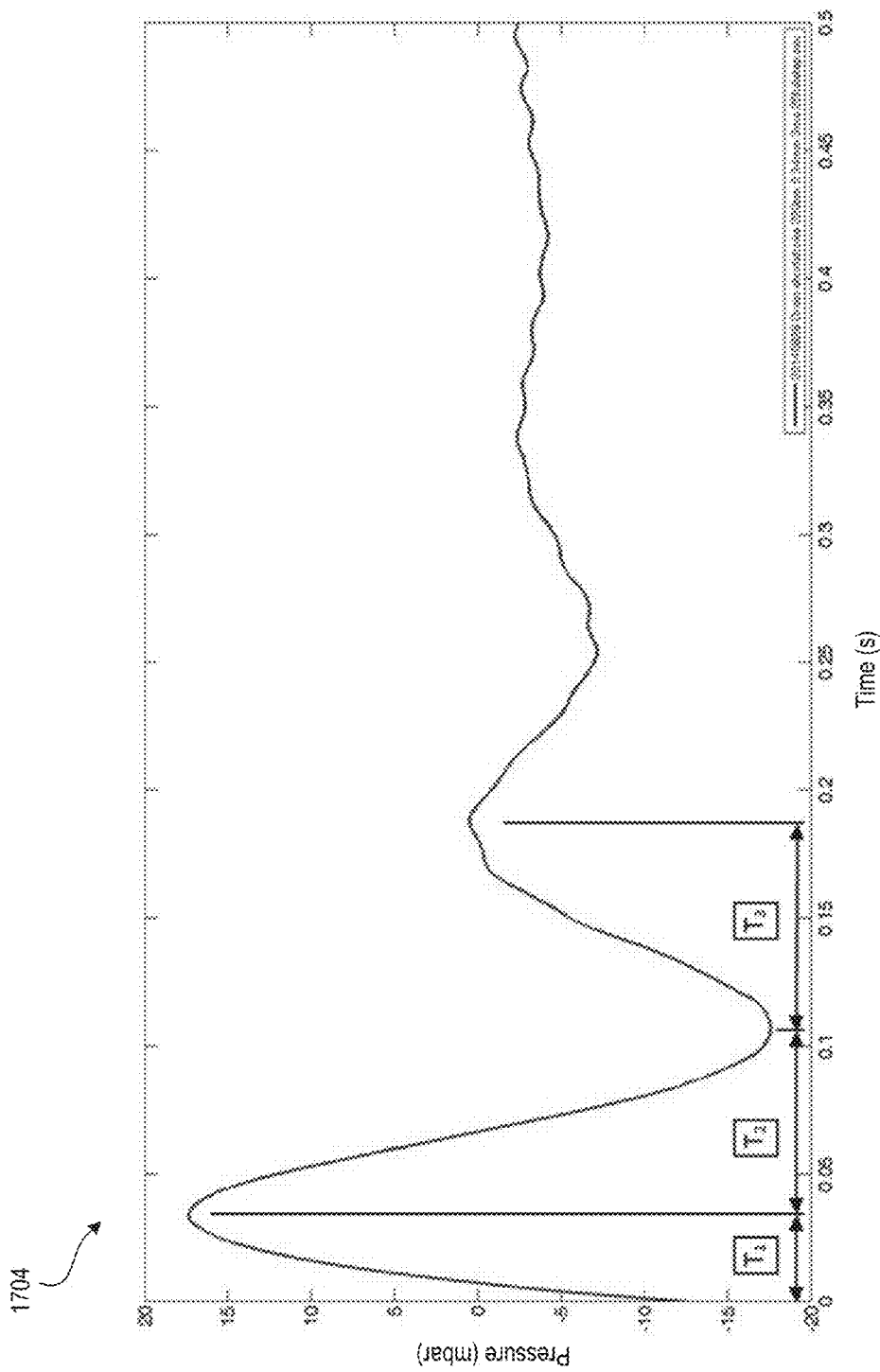
FIG. 17B shows a pressure waveform that includes a processed version of the data of FIG. 17A.

FIG. 17B shows a pressure waveform 1704 that includes the data of FIG. 17A after being smoothed and after having the background curve subtracted. The waveform 904 has a relatively more symmetrical pattern as compared to the waveform 1702 of FIG. 17A, thereby enabling a more accurate evaluation of the oscillation period T.

The data shown in FIGS. 17A and 17B correspond to the short-stroke test performed with a dispensed water volume of 0.33 cubic centimeters at a fixed rate of 4.4 milliliters per second for an occlusion 1408 positioned at a distance x=220 centimeters along the patient line 1430. Data was also obtained for various other cassette 112/occlusion 1408 configurations at various different distances x for the occlusion 1408. For example, 15 different cassette-occlusion combinations were used, for both internal and external partial occlusions, and each combination was tested at 5-8 different distances x for the occlusion 1408. For each test, the period T of the resulting oscillations was evaluated using at least three different methods: i) first half-wave period; ii) other half- and full-wave periods; and iii) Fast Fourier Transform. It was determined that the first half-wave period method achieved the greatest sensitivity and specificity for determining the distance x of the occlusion 1408.

Sensitivity and specificity are statistical measures of the performance of the detection method. The sensitivity, also referred to as the true positive rate, measures the proportion of positives that are correctly identified as such. In this context, the sensitivity may correspond to the ability of the system to correctly identify occlusions (e.g., for distances x within a particular range). The specificity, also referred to as the true negative rate, measures the proportion of negatives that are correctly identified as such. In this context, the specificity may correspond to the accuracy of the detection method (e.g., the margin of error of determined distances x).

The first half-wave period is the time measurement from the end of the pump motion to a first local extremum of the pressure measurements, represented by $T_1$ in FIG. 17B. For drain-direction flow, the first local extremum is a local maximum. As compared to latter half-waves (e.g., $T_2$ and $T_3$), sensitivity and specificity benefit from certain features of the first half-wave. For example, onset is relatively precise because it is well defined by the cessation of the pump motion (e.g., during short-stroke testing), the timing of which can be measurable with high precision. Further, completion of the first half-wave can be measured with a relatively high signal-to-noise ratio due to the signal maximization and the noise minimization associated with the first half-wave period. For example, the first half-wave presents the elastic wave with its maximum amplitude, which maximizes the precision of measuring the extremum that defines its endpoint by minimizing the effect of various sources of noise on the measurement. After the first half-wave, a rapid decay of amplitude in the subsequent oscillations occurs due to viscoelastic effects and the effects of partial wave reflection (e.g., as described above with reference to Equation 6). Further, subsequent wave reflections may generate additional sources of noise due to constructive and destructive interference of partially transmitted waves. The effects of such noise do not manifest in the first half-wave period.

The latter half-wave periods (e.g., the second half-wave period $T_2$ and the third half-wave period $T_3$) appear to have substantially equal durations (e.g., as might be expected of a naturally resonating wave), while the first half-wave period $T_1$ appears to be relatively shorter (e.g., because the first half-wave period $T_1$ is the incipient period upon impulsively starting the elastic wave). Thus, it was not obvious a priori that the half-wave period $T_1$ would correlate well with the distance x of the occlusion 1408. However, use of the first half-wave produced the best sensitivity and specificity in the analyses performed.

As the name implies, because the first half-wave period $T_1$ only represents half of the period T of the oscillations, the first half-wave period $T_1$ corresponds to the transit time of the elastic wave from the pressure sensor 151A to the location of the occlusion 1408 (e.g., not the full round-trip transit time T). Thus, when using the first half-wave period $T_1$ to determine the distance x to the occlusion 1408, Equation 1 can be simplified as Equation 13:

$$X=T_1 * c_o \quad (13)$$

where $T_1$ is the first half-wave period, $c_o$ is the propagation speed of the elastic waves, and x is the distance along the conduit from the location of the pressure sensor 151A to the location of the occlusion 1408.

Figure 18:
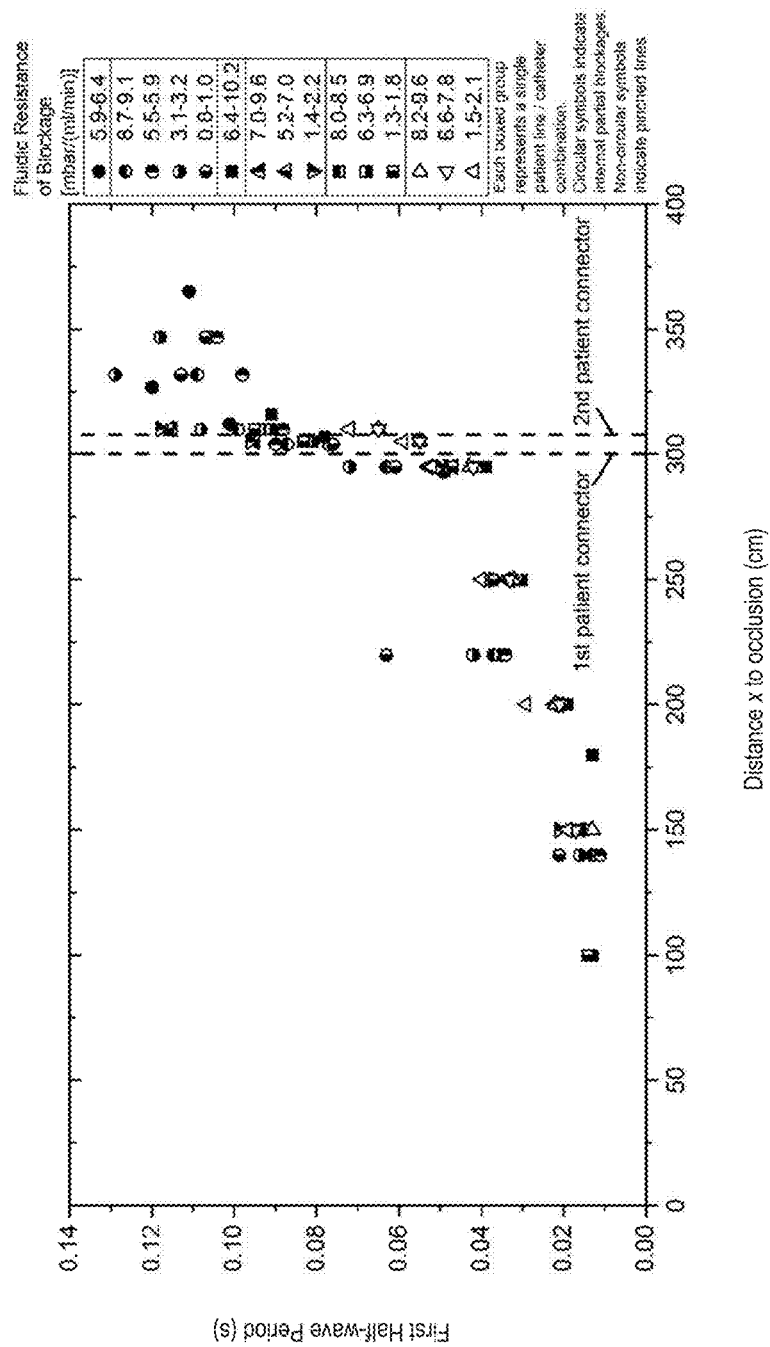
FIG. 18 shows a representative graph of first half-wave periods of elastic wave oscillations.

FIG. 18 shows a representative graph of the first half-wave periods of the oscillations (in seconds) versus the various distances x of the occlusions 1408 (in centimeters) for the 15 different cassette-occlusion combinations. The occlusions 1408, of both the internal and external types, were located at various distances x that correspond to positions along the patient line 1430 (e.g., x=60, 100, 140, 150, 180, 200, 220, 250 centimeters), distances x that correspond to positions between the patient connectors of the port 1404 (e.g., x=304-307 centimeters), and distances that correspond to positions along the catheter 1402 (e.g., x=310-365 centimeters). The occlusions 1408 had various fluidic resistance $R_f$ values (e.g., $R_f$=5.9-6.4, 8.7-9.1, 5.5-5.9, 3.1-3.2, 0.8-1.0, 6.4-10.2, 7.0-9.6, 5.2-7.0, 1.4-2.2, 8.0-8.5, 6.3-6.9, 1.3-1.8, 8.2-9.6, 6.6-7.8, and 1.5-2.1 mbar/(ml/min)).

Among the distances x tested, evaluation of the first half-wave period resulted in sensitivity (e.g., the ability to correctly identify occlusions) for distances x greater than or equal to approximately 100 centimeters. In some examples, for distances x of less than 100 centimeters, the local maxima of the pressure measurements may be undetectable. The range of sensitivity may be extended to lower distance values x by increasing the strength of the pressure impulse and/or by implementing additional or alternate signal processing of the pressure waveforms (e.g., 1702, 1704 of FIGS. 17A and 17B).

Recalling that the goal of this experiment was to determine whether the detection method can provide a measurement of the distance x of the occlusion 1408 that is sensitive and specific for the distance x but insensitive to the type of restriction or the value of the fluidic resistance $R_f$ of the occlusion 1408, the first half-wave periods corresponding to each distance x would ideally be identical. However, the vertical scatter seen in the data of FIG. 18 implies a specificity (e.g., an accuracy) of approximately ±40 centimeters. In some implementations, the detection method may be employed to determine in which of five sections/zones the occlusion 1408 is located. For example, the detection method can be used to determine whether the occlusion 1408 is located in a first zone of the patient line 1430 (e.g., approximately x=0-100 centimeters), in a second zone of the patient line 1430 (e.g., approximately x=100-200 centimeters), in a third zone of the patient line 1430 (e.g., approximately x=200-295 centimeters), between the patient connectors of the port 1404 (e.g., approximately x=304-307 centimeters), or in the catheter 1402 (e.g., approximately x=310-365 centimeters).

While the detection method described above largely focuses on using the first half-wave period for evaluating the period T of the oscillations, other methods can be employed. For example, the second half-wave period or the third half-wave period (e.g., $T_2$ and $T_3$, respectively, as shown in FIG. 17B) can be evaluated. Alternatively, frequency-based signal analyses (e.g., Fast Fourier Transform) may be used to determine the distance to the occlusion x.

Figure 19:
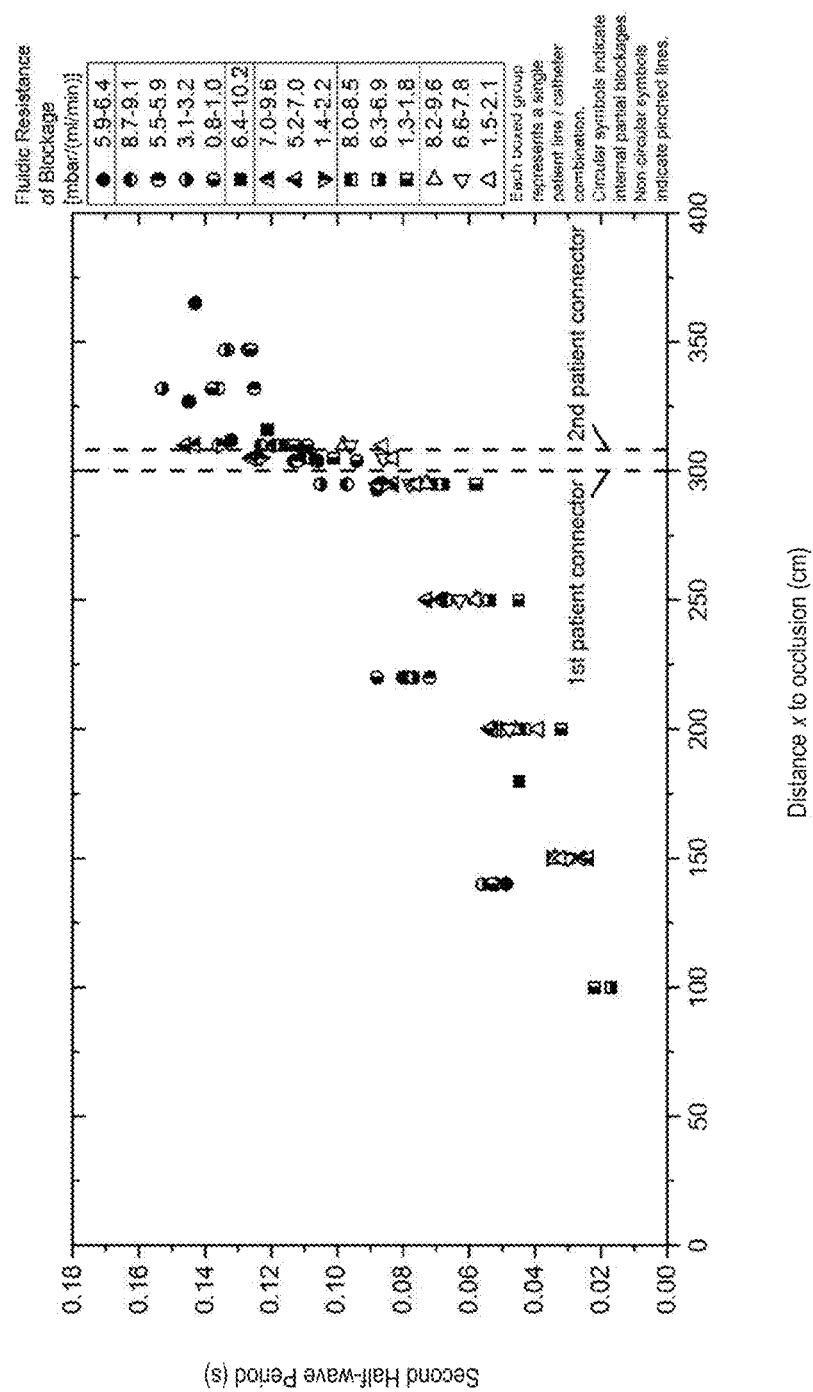
FIG. 19 shows a representative graph of second half-wave periods of elastic wave oscillations.
Figure 20:
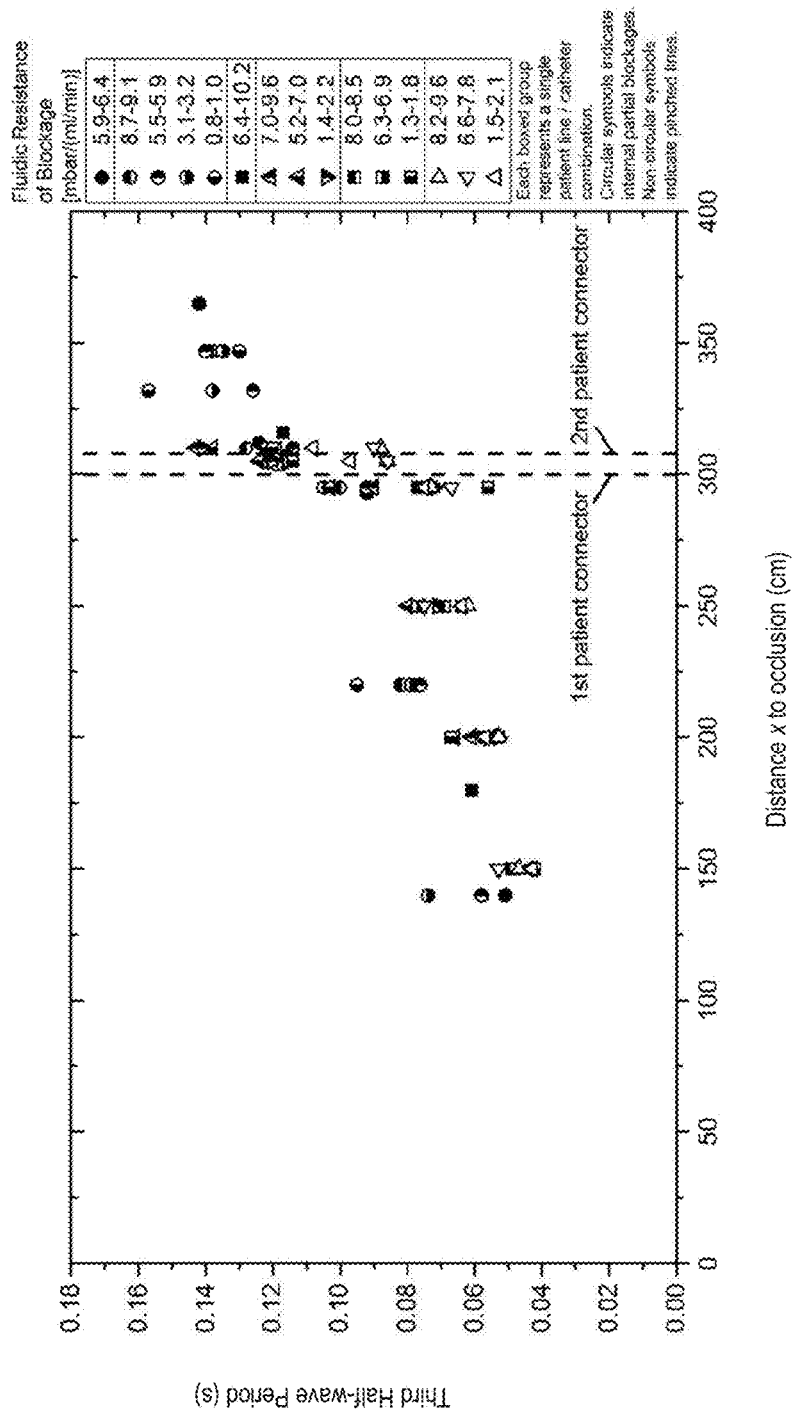
FIG. 20 shows a representative graph of third half-wave periods of elastic wave oscillations.

FIG. 19 shows a representative graph of the second half-wave periods of the oscillation (in seconds) versus the various distances x of the occlusions 1408 (in centimeters) for the 15 different cassette-occlusion combinations, and FIG. 20 shows a representative graph of the third half-wave periods of the oscillation (in seconds) versus the various distances x of the occlusions 1408 (in centimeters) for the 15 different cassette-occlusion combinations. Both graphs show a larger degree of vertical scatter as compared to the vertical scatter present in the data of FIG. 18, and thus indicate reduced specificity, for the reasons discussed above with respect to FIG. 17B.

In some implementations, the Fast Fourier Transform (FFT) of the pressure waveform can be used to evaluate the period T of the oscillations. For example, the pressure waveform (e.g., 1702, 1704 of FIGS. 17A and 17B) can be transformed into the frequency domain, and the transform can be evaluated to determine the period T of the oscillations. However, a limited number of wave periods transpiring prior to the substantially full decay of the wave amplitude may result in imprecision in the frequency space (e.g., due to the relatively short window in the time domain), thereby resulting in diminished sensitivity and/or specificity.

In some implementations, the specificity is improved (e.g., the vertical scatter of the data is reduced) by employing additional signal processing to enhance the accuracy of the wave period measurement. In some implementations, the specificity is improved by performing a pre-test calibration routine to account for any cassette- or medical tube/patient line-specific variations in the wave period versus the distance x.

Figure 21:
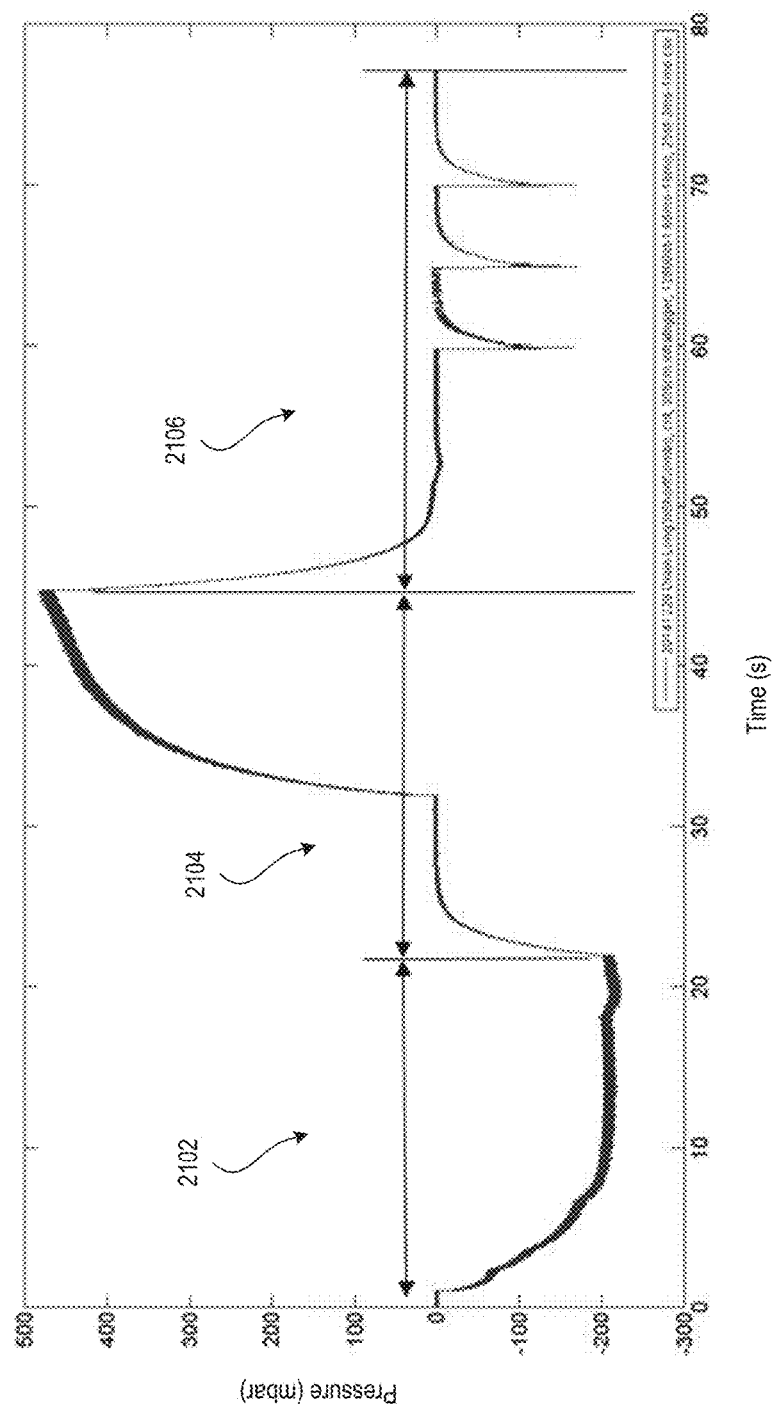
FIG. 21 shows a pressure waveform that includes pressure measurements over time while performing multiple short-stroke tests.

In some implementations, the specificity of the detection method is improved by performing multiple short-stroke tests and averaging the results. For example, referring to FIG. 21, a long-stroke test may be initially performed (e.g., in the drain direction) during a first phase 2102 in which the pump moves at a constant speed corresponding to a flow rate of Q=30 milliliters per minute. During the first phase 2102, the pump is withdrawn and fluid is pulled from the patient line 1430 into the pump cylinder. The long-stroke test may be initially performed to adjust the configuration of a partial external occlusion (e.g., as shown in FIG. 16) in order to achieve the desired fluidic resistance before performing the series of short-stroke tests. The initial mean pressure value may be subtracted from the pressure measurements. The steady-state pressure is used for determining the fluidic resistance $R_f$ of the total flowpath. If the fluidic resistance $R_f$ exceeds a threshold value (e.g., a predetermined threshold value), multiple short-stroke tests are performed to determine the location of the occlusion. During a second phase 2104, the pump may be returned to position for the start of the short-stroke tests; however, in some implementations, the pump is not returned to position (e.g., to avoid reversal of flow during detection). The second phase 2104 begins with a pause to allow transients to complete, followed by a long pump-stroke in the fill direction (e.g., fluid is pumped from the pump cylinder into the patient line 1430). During a third phase 2106, the multiple short-stroke tests are then performed. The resulting pressure measurements, as well as any analyses performed to determine the location of the occlusion x, can be averaged to reduce the uncertainty, thereby improving the specificity of the detection method.

While the detection method has been largely described as being implemented in a testing environment, similar techniques can be employed for detecting occlusions in the conduit when the patient line is attached to a patient receiving a dialysis treatment (e.g., as shown in FIG. 10). For example, the detection method can be employed for determining the distance x of the occlusion 1008 in the conduit by measuring the period T of elastic wave oscillations generated in the patient line 130 itself. In particular, the propagation speed $c_o$ of the elastic waves generated in a particular system configuration can be determined according to Equation 1 in advance of a treatment by positioning a test occlusion at a known distance x and measuring the period T of the oscillations—that is, each specific cassette-patient line-port-catheter combination may be "calibrated" prior to use. Once the propagation speed $c_o$ for the system is known, the period T of oscillations can be measured during an actual dialysis treatment, and Equation 1 can be used to determine the distance x of the occlusion 1008. Alternatively, an experimentally determined correlation between the period T and the distance x of the occlusion 1008 may be used. The type of the occlusion 1008 can then be inferred based on the determined location of the occlusion 1008, as described above.

While the dialysis system has been largely described as being a peritoneal dialysis (PD) system, other medical treatment systems can employ the techniques described herein. Examples of other medical treatment systems include hemodialysis systems, hemofiltration systems, hemodiafiltration systems, apheresis systems, and cardiopulmonary bypass systems.

Figure 22:
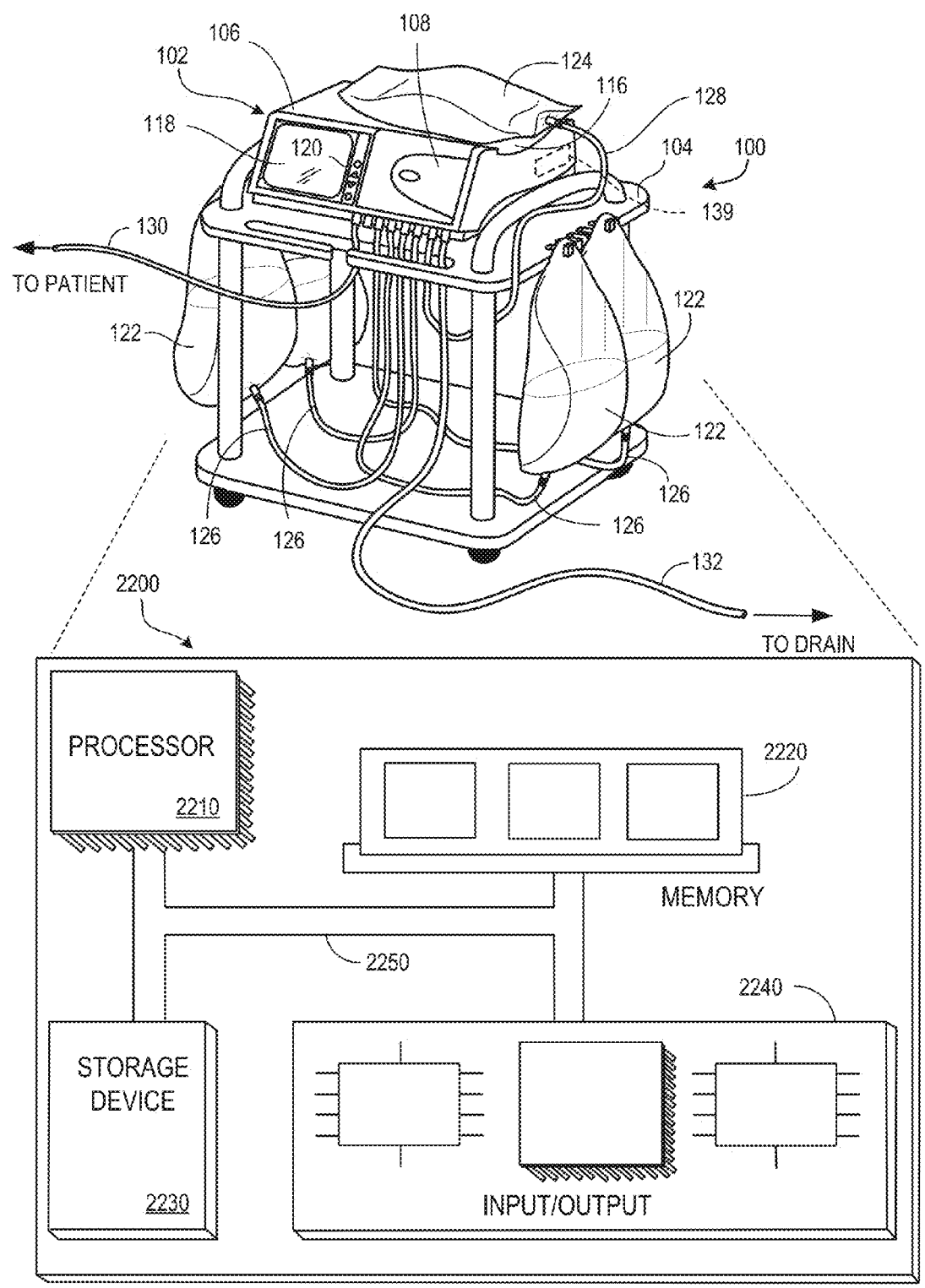
FIG. 22 shows a computer system and related components.

FIG. 22 is a block diagram of an example computer system 2200. For example, the control unit (139 of FIG. 1), the computing device (1434 of FIG. 14), and/or the microcontroller (1436 of FIG. 14) could be examples of the system 2200 described here. The system 2200 includes a processor 2210, a memory 2220, a storage device 2230, and an input/output device 2240. Each of the components 2210, 2220, 2230, and 2240 can be interconnected, for example, using a system bus 2250. The processor 2210 is capable of processing instructions for execution within the system 2200. The processor 2210 can be a single-threaded processor, a multi-threaded processor, or a quantum computer. The processor 2210 is capable of processing instructions stored in the memory 2220 or on the storage device 2230. The processor 2210 may execute operations such as causing the dialysis system to carry out dialysis functions.

The memory 2220 stores information within the system 2200. In some implementations, the memory 2220 is a computer-readable medium. The memory 2220 can, for example, be a volatile memory unit or a non-volatile memory unit. In some implementations, the memory 2220 stores information (e.g., executable code) for causing the pumps of the dialysis system to operate as described herein.

The storage device 2230 is capable of providing mass storage for the system 2200. In some implementations, the storage device 2230 is a non-transitory computer-readable medium. The storage device 2230 can include, for example, a hard disk device, an optical disk device, a solid-date drive, a flash drive, magnetic tape, or some other large capacity storage device. The storage device 2230 may alternatively be a cloud storage device, e.g., a logical storage device including multiple physical storage devices distributed on a network and accessed using a network.

The input/output device 2240 provides input/output operations for the system 2200. In some implementations, the input/output device 2240 includes one or more of network interface devices (e.g., an Ethernet card), a serial communication device (e.g., an RS-232 port), and/or a wireless interface device (e.g., an 802.11 card, a 3G wireless modem, or a 4G wireless modem). In some implementations, the input/output device 2240 may include short-range wireless transmission and receiving components, such as Wi-Fi, Bluetooth, and/or near field communication (NFC) components, among others. In some implementations, the input/output device includes driver devices configured to receive input data and send output data to other input/output devices, e.g., keyboard, printer and display devices (such as the touch screen display 118). In some implementations, mobile computing devices, mobile communication devices, and other devices are used.

In some implementations, the system 2200 is a microcontroller (e.g., the microcontroller 1436 of FIG. 14). A microcontroller is a device that contains multiple elements of a computer system in a single electronics package. For example, the single electronics package could contain the processor 2210, the memory 2220, the storage device 2230, and input/output devices 2240.

Although an example processing system has been described in FIG. 22, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:

1. A method comprising:
   measuring a first pressure at a proximal end of a medical tube connected to a dialysis machine;
   measuring a second pressure at the proximal end of the medical tube;
   determining an elapsed time between the first pressure measurement and the second pressure measurement; and
   determining a location of an occlusion in the medical tube based on the elapsed time.

2. The method of claim 1, wherein the dialysis machine comprises a peritoneal dialysis (PD) machine.

3. The method of claim 1, wherein at least one of the first pressure and the second pressure comprises a local extremum of pressure measurements at the proximal end of the medical tube.

4. The method of claim 3, wherein the local extremum comprises at least one of a local maximum and a local minimum.

5. The method of claim 1, wherein the first pressure and the second pressure are measured by a pressure sensor mounted at the proximal end of the medical tube.

6. The method of claim 1, wherein the elapsed time represents a period of oscillations of an elastic wave.

7. The method of claim 6, comprising determining the location of the occlusion in the medical tube based on the elapsed time and a wave speed of the elastic wave.

8. The method of claim 7, wherein the wave speed of the elastic wave is based on one or more of dimensions of the medical tube, a material composition of the medical tube, and a density of a fluid flowing through the medical tube.

9. The method of claim 7, wherein the wave speed of the elastic wave is empirically determined.

10. The method of claim 6, wherein the elastic wave originates from the proximal end of the medical tube.

11. The method of claim 6, wherein the elastic wave is generated in response to at least one of an increase and a decrease in pressure in the medical tube.

12. The method of claim 11, wherein the at least one of an increase and a decrease in pressure is in response to a motion of a pump of the dialysis machine.

13. The method of claim 6, wherein a fluid flowing through the medical tube is at least partially blocked by the occlusion.

14. The method of claim 13, wherein the fluid being at least partially blocked by the occlusion causes an increase or a decrease in pressure in the medical tube.

15. The method of claim 6, wherein the oscillations of the elastic wave are caused at least in part by the elastic wave being reflected back from the location of the occlusion.

16. The method of claim 1, wherein the medical tube comprises a catheter at a distal end of the medical tube.

17. The method of claim 1, comprising inferring a type of the occlusion based at least in part on the determined location of the occlusion.

18. The method of claim 17, wherein the type of the occlusion comprises one or more of a pinch of the medical tube, a kink in the medical tube, a deposit in the medical tube, and a deposit blocking a hole of a catheter at a distal end of the medical tube.

19. The method of claim 18, wherein the deposit comprises omental fat.

20. The method of claim 1, comprising performing a calibration prior to determining the location of the occlusion, the calibration for determining a wave speed of an elastic wave propagating through the medical tube.

21. The method of claim 20, wherein the calibration is for determining the wave speed of the elastic wave propagating through the medical tube for a particular medical tube and cassette configuration used in the dialysis machine.

22. A method comprising:
measuring a plurality of pressures at a proximal end of a medical tube connected to a dialysis machine;
determining one or more elapsed times between local extrema of the measured pressures; and
determining a location of an occlusion in the medical tube based on the one or more elapsed times.

23. The method of claim 22, wherein the local extrema comprise at least one of a local maximum and a local minimum.

24. The method of claim 22, comprising removing noise components from the measured pressures before determining the local extrema of the measured pressures.

25. The method of claim 22, wherein magnitudes of the pressure measurements decay over time when the occlusion is a partial occlusion.

26. The method of claim 25, comprising subtracting, from the measured pressures, values that approximate the decay of the pressure measurements as a result of the occlusion being a partial occlusion before determining the local extrema.

27. The method of claim 22, wherein at least one of the local extrema of the measured pressures corresponds to an end of a pump motion that causes fluid to flow through the medical tube.

28. The method of claim 27, comprising:
determining an elapsed time between i) the end of the pump motion, and ii) an occurrence of a local extrema that occurs after the end of the pump motion; and
determining the location of the occlusion based on the elapsed time.

29. The method of claim 28, wherein the elapsed time represents a first half-wave period of oscillations of an elastic wave generated in response to at least one of an increase and a decrease in pressure in the medical tube.

30. The method of claim 22, comprising performing one or more signal processing techniques on the measured pressures.

31. A method comprising:
measuring a first pressure at a proximal end of a medical tube connected to a dialysis machine, the medical tube comprising a plurality of zones;
measuring a second pressure at the proximal end of the medical tube;
determining an elapsed time between the first pressure measurement and the second pressure measurement; and
determining in which of the plurality of zones an occlusion is located based on the elapsed time.

32. The method of claim 31, wherein the medical tube comprises five zones.

33. The method of claim 31, wherein the medical tube comprises a catheter at a distal end of the medical tube, and at least one of the zones comprises the catheter.

34. The method of claim 33, wherein the medical tube comprises a port connecting the catheter to the medical tube, and at least one of the zones comprises the port.

35. A dialysis machine comprising:
a medical tube having a proximal end connected to an outlet of the dialysis machine;
a pressure sensor mounted at the proximal end of the medical tube, the pressure sensor configured for measuring a first and second pressure at the proximal end of the medical tube; and
a processor configured for:
determining an elapsed time between the first pressure measurement and the second pressure measurement; and
determining a location of an occlusion in the medical tube based on the elapsed time.

36. The dialysis machine of claim 35, wherein the dialysis machine comprises a peritoneal dialysis machine.

* * * * *